(12) United States Patent
Ahn et al.

(10) Patent No.: US 11,091,741 B2
(45) Date of Patent: Aug. 17, 2021

(54) METHOD FOR PRODUCING MEDIUM CHAIN DIOL

(71) Applicant: KOREA RESEARCH INSTITUTE OF BIOSCIENCE AND BIOTECHNOLOGY, Daejeon (KR)

(72) Inventors: Jung Oh Ahn, Daejeon (KR); Hong Weon Lee, Daejeon (KR); Min Jeong Jang, Daejeon (KR); Chun Sug Kim, Daejeon (KR); Gyu Yeon Park, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 81 days.

(21) Appl. No.: 15/771,799

(22) PCT Filed: Oct. 27, 2016

(86) PCT No.: PCT/KR2016/012170
§ 371 (c)(1),
(2) Date: Apr. 27, 2018

(87) PCT Pub. No.: WO2017/074061
PCT Pub. Date: May 4, 2017

(65) Prior Publication Data
US 2018/0340195 A1    Nov. 29, 2018

(30) Foreign Application Priority Data

Oct. 27, 2015  (KR) .................. 10-2015-0149251
Oct. 27, 2016  (KR) .................. 10-2016-0141017

(51) Int. Cl.
*C12N 9/04*    (2006.01)
*C12N 9/06*    (2006.01)
(Continued)

(52) U.S. Cl.
CPC ........... *C12N 9/0006* (2013.01); *C12N 9/001* (2013.01); *C12N 9/0008* (2013.01); *C12N 15/81* (2013.01);
(Continued)

(58) Field of Classification Search
CPC .... C12N 9/001; C12N 9/0006; C12N 9/0008; C12P 7/18
See application file for complete search history.

(56) References Cited

U.S. PATENT DOCUMENTS 8,530,206 B2     9/2013  Develter et al.
10,640,796 B2 *  5/2020  Gatter ................... C12P 7/6409
(Continued)

FOREIGN PATENT DOCUMENTS

DE    102014220186 A1    6/2015
KR    10-1145405 B       5/2012
(Continued)

OTHER PUBLICATIONS

GenBank. ADH1, ADH2, ADH3, ADH4, ADH5, ADH5, ADH7, FADH, FALDH1, FALDH2, FALDH3, FALDH4, POX1, POX2, POX3, POX4, POX5, & POX6. retrieved via https://www.ncbi.nlm.nih.gov/nucleotide/ on Sep. 16, 2020.*

(Continued)

*Primary Examiner* — Yong D Pak
(74) *Attorney, Agent, or Firm* — Merchant & Gould P.C.

(57) ABSTRACT

The present invention relates to a method for producing medium chain diol and, more particularly to recombinant microorganisms in which fatty alcohol dehydrogenase and/or fatty alcohol oxidase genes on a ω-oxidative metabolism pathway are deleted, the fatty aldehyde dehydrogenase genes are optionally deleted, and β-oxidative metabolism pathway-related genes are deleted, and to a method for producing medium chain diol from fatty acid-derived alco- (Continued)

hol or alkane by culturing the recombinant microorganisms. The recombinant microorganisms of the present invention can produce a high yield of medium chain diol by preventing further oxidation and β-oxidative metabolism of fatty alcohols.

14 Claims, 8 Drawing Sheets

Specification includes a Sequence Listing.

(51) Int. Cl.
    *C12P 7/18*     (2006.01)
    *C12N 1/14*     (2006.01)
    *C12N 15/00*     (2006.01)
    *C12N 15/81*     (2006.01)
    *C12N 9/02*     (2006.01)
    *C07H 21/04*     (2006.01)
    *C12N 1/18*     (2006.01)

(52) U.S. Cl.
    CPC ................ *C12P 7/18* (2013.01); *C07H 21/04* (2013.01); *C12N 1/18* (2013.01)

(56) References Cited

U.S. PATENT DOCUMENTS

2015/0111268 A1     4/2015     Park et al.
2015/0167027 A1     6/2015     Seo et al.
2016/0304913 A1     10/2016     Gatter et al.

FOREIGN PATENT DOCUMENTS

| KR | 10-2012-0107021 A | 9/2012 | |
|---|---|---|---|
| KR | 10-2012-0128776 A | 11/2012 | |
| KR | 10-2014-0142518 A | 12/2014 | |
| KR | 10-2015-0039055 A | 4/2015 | |
| KR | 10-2015-0068581 A | 6/2015 | |
| WO | 2014/201474 A1 | 12/2014 | |
| WO | WO-2015086684 A1 * | 6/2015 | ............. C12N 9/001 |

OTHER PUBLICATIONS

Int'l Search Report from Int'l Appl'n No. PCT/KR2016/012170, dated Jan. 17, 2017.
Written Opinion from Int'l Appl'n No. PCT/KR2016/012170, dated Jan. 17, 2017.
Park et al., "Metabolic Engineering of *Escherichia coli* for the Production of Medium-chain-length Polyhydroxyalkanoates Rich in Specific Monomers", FEMS Microbiology Letters, vol. 214, pp. 217-222 (2002).
Extended European Search Report from European Application No. 16860244.9, dated Sep. 21, 2018.
Gatter, M. et al., "A newly identified fatty alcohol oxidase gene is mainly responsible for the oxidation of long-chain ω-hydroxy fatty acids in Yarrowia lipolytica", FEMS Yeast Res, 14: 858-872 (2014).

* cited by examiner

| Genotype (with Phenotype) | ACO 1 | ACO 2 | ACO 3 | ACO 4 | ACO 5 | ACO 6 | FALDH 1 | FALDH 2 | FALDH 3 | FALDH 4 | FAO | ADH 1 | ADH 2 | ADH 3 | ADH 4 | ADH 5 | ADH 6 | ADH 7 | ADH 8 | FADH | cell stock No. |
|---|---|---|---|---|---|---|---|---|---|---|---|---|---|---|---|---|---|---|---|---|---|
| MatA, leu2-270, ura3-302::Δleu2 | | | | | | | | | | | | | | | | | | | | | WT |
| MatA, leu2-270, ura3-302::Δaco3Δaco3Δku70Δaco5 Δaco4Δaco6Δaco1Δaco2::LEU2 | x | x | x | x | x | x | | | | | | | | | | | | | | | Y1-11 |
| MatA, leu2-270, ura3-302::Δ aco1-6Δura3Δku70ΔFA LDH1-4::LEU2 | x | x | x | x | x | x | x | x | x | x | | | | | | | | | | | Y1-28 |
| MatA, leu2-270, ura3-302::Δ aco1-6Δura3Δku70ΔFA LDH1-4ΔFAO::LEU2 | x | x | x | x | x | x | x | x | x | x | x | | | | | | | | | | Y1-36 |
| MatA, leu2-270, ura3-302::Δ aco1-6Δura3Δku70ΔFALD H1-4ΔFAOΔADH1-8::LEU2 | x | x | x | x | x | x | x | x | x | x | x | x | x | x | x | x | x | x | x | | Y4-2 |
| MatA, leu2-270, ura3-302::Δ aco1-6Δura3Δku70ΔFAD H1-4ΔFAOΔADH1-8Δfadh::LEU2 | x | x | x | x | x | x | x | x | x | x | x | x | x | x | x | x | x | x | x | x | Y4-20 |

FIG. 5

(a) Standard sample
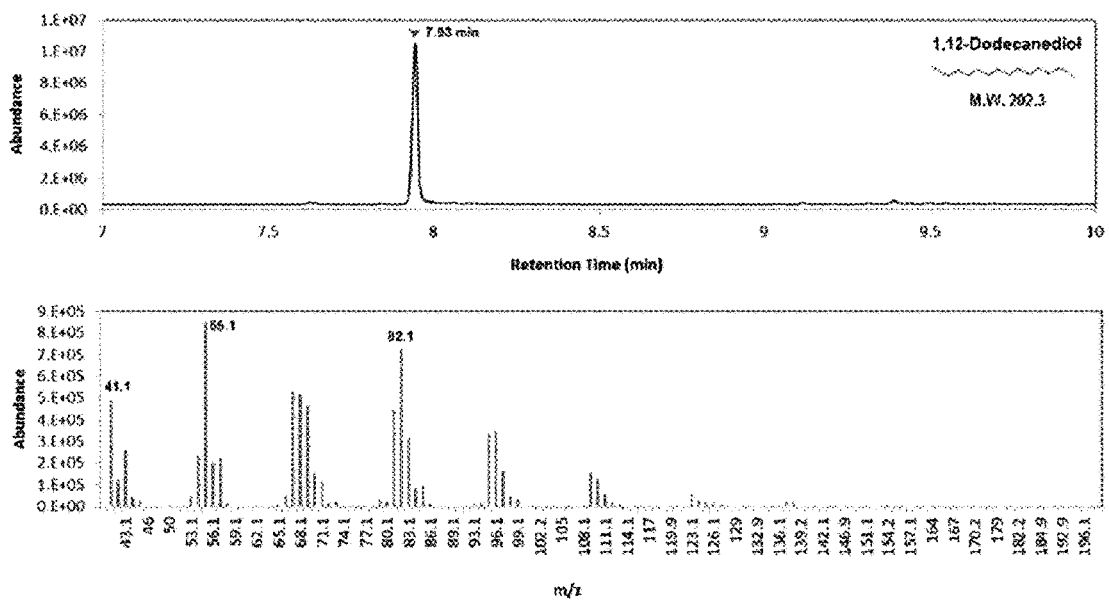
(b) Culture broth sample
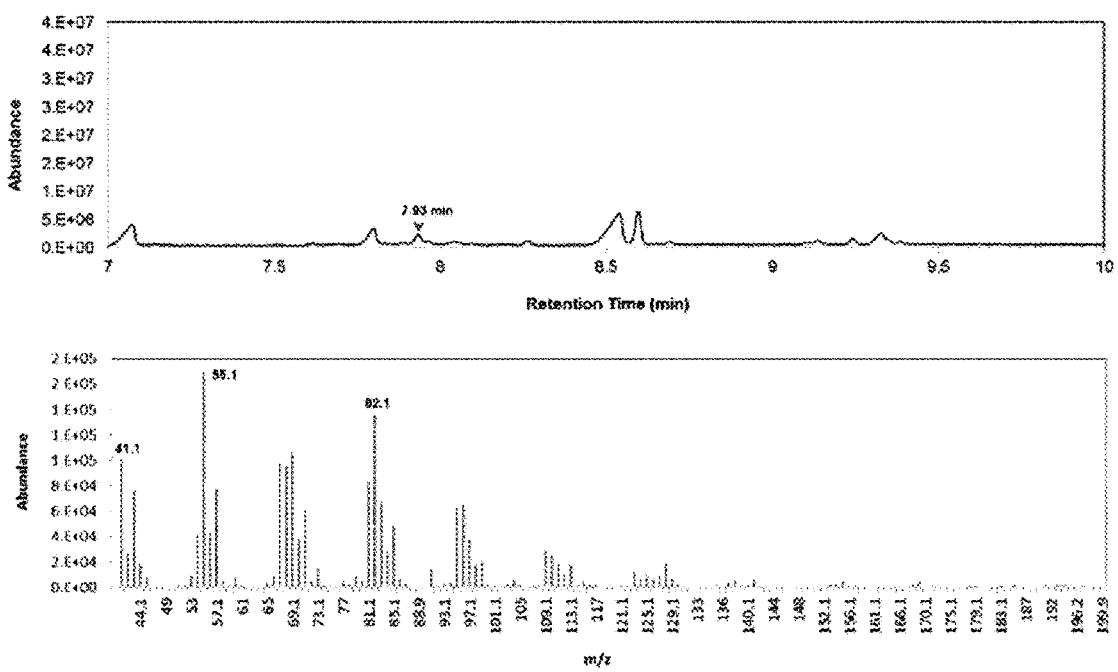
FIG.8

METHOD FOR PRODUCING MEDIUM CHAIN DIOL

This application is a National Stage Application of PCT/KR2016/012170, filed 27 Oct. 2016, which claims benefit of Serial No. 10-2016-0141017, filed 27 Oct. 2016 in Korea and Serial No. 10-2015-0149251, filed 27 Oct. 2015 in Korea and which applications are incorporated herein by reference. To the extent appropriate, a claim of priority is made to each of the above disclosed applications.

TECHNICAL FIELD

The present invention relates to a method for producing a medium chain diol, and more particularly, to a method for producing a medium chain diol from a fatty acid-derived alcohol or alkane by culturing a recombinant microorganism from which fatty alcohol dehydrogenase and/or fatty alcohol oxidase genes in an ω-oxidative metabolism pathway are deleted, a fatty aldehyde dehydrogenase gene is optionally deleted, and β-oxidative metabolism pathway-related genes are also deleted.

BACKGROUND ART

Bioplatform compounds are produced through biological or chemical conversion on the basis of biomass-derived raw materials, and have been used for synthesis of polymeric monomers, new materials, and the like.

Among the bioplatform compounds, a medium chain diol is a material used as a monomer for polyesters. In this case, the polyesters have been used for various applications including fibers, films, and combinations thereof due to their excellent properties. For example, the polyethylene terephthalate obtained through the polycondensation of terephthalic acid with ethylene glycol has been used for many applications due to excellent physical properties such as mechanical strength, chemical properties, and the like, and has been mass-produced as a synthetic fiber most suitable for clothing all over the world. Also, the market for polytrimethylene terephthalate prepared using 1,3-propanediol and terephthalic acid as raw materials tends to increase with the recent development of inexpensive methods of synthesizing 1,3-propanediol. Thus, the polytrimethylene terephthalate is expected to be employed for clothing applications requiring the soft texture because it has polymeric characteristics such as excellent elastic recovery percentage of elongation and low Young's modulus. In addition, the biomass resource-derived polyesters have come into the spotlight for fear of the rising price and depletion of petroleum resources.

Production of medium chain diols may be carried out using biological methods through chemical synthesis or microbial fermentation. In this case, the use of such biological methods requires the development of novel strains and the optimization of fermentation processes using metabolic engineering technology.

In the prior art, a microorganism which harbors a β-oxidative metabolism pathway as well as an ω-oxidative metabolism pathway may be used as the strain capable of producing a medium chain diol. For example, it is known that the strains such as *Klebsiella oxytoca, Klebsiella pneumoniae, Aerobacter aerogenes*, recombinant *Saccharomyces cerevisiae*, and the like may produce 2,3-butanediol with high yield and high productivity (Korean Patent Publication Nos. 10-2012-107021, 10-2012-0128776, and 10-2015-0068581). However, because some of these microorganisms are classified into pathogenic microorganisms, they have limitations in terms of safety and industrialization. Also, because the medium chain diols correspond to intermediate products in the ω-oxidative metabolism pathway, the medium chain diols have a problem in that the medium chain diols may not be produced with high yield when they are produced using the microorganisms.

DISCLOSURE

Technical Problem

Therefore, it is an object of the present invention to provide a recombinant microorganism from which fatty alcohol dehydrogenase and/or fatty alcohol oxidase-related genes in an ω-oxidative metabolism pathway are deleted, a fatty aldehyde dehydrogenase gene is optionally deleted, and β-oxidative metabolism pathway-related genes are also deleted, and a method of producing a medium chain diol from a fatty acid-derived alcohol or alkane by culturing the recombinant microorganism.

Technical Solution

To solve the above problems, according to an aspect of the present invention, there is provided a recombinant microorganism from which one or more genes selected from the group consisting of fatty alcohol dehydrogenase and fatty alcohol oxidase genes in an ω-oxidative metabolism pathway are deleted, a fatty aldehyde dehydrogenase gene is optionally deleted, and β-oxidative metabolism pathway-related genes are also deleted.

According to an embodiment of the present invention, the fatty alcohol dehydrogenase gene, the fatty alcohol oxidase gene, the fatty aldehyde dehydrogenase gene, and the β-oxidative metabolism pathway-related genes may be deleted from all homologous genes present in the microorganism, but the present invention is not limited thereto. According to another embodiment of the present invention, the fatty alcohol dehydrogenase gene, the fatty alcohol oxidase gene, the fatty aldehyde dehydrogenase gene, and the β-oxidative metabolism pathway-related genes may be deleted from some of the homologous genes present in the corresponding microorganism, but the present invention is not limited thereto.

According to an embodiment of the present invention, the fatty alcohol dehydrogenase gene may be selected from the group consisting of ADH1, ADH2, ADH3, ADH4, ADH5, ADH6, ADH7, ADH8, and FADH genes, but the present invention is not limited thereto. According to another embodiment of the present invention, the fatty alcohol oxidase gene may be an FAO gene, but the present invention is not limited thereto. According to still another embodiment of the present invention, the fatty aldehyde dehydrogenase gene may be a gene selected from the group consisting of FALDH1, FALDH2, FALDH3, and FALDH4 genes, but the present invention is not limited thereto.

According to an embodiment of the present invention, the β-oxidative metabolism pathway-related genes may be an acyl-CoA oxidase gene, but the present invention is not limited thereto. According to preferred embodiments of the present invention, the acyl-CoA oxidase gene may be selected from the group consisting of ACO1, ACO2, ACO3, ACO4, ACO5, and ACO6 genes, but the present invention is not limited thereto.

According to an embodiment of the present invention, the microorganism may be a yeast or *Escherichia coli*, but the present invention is not limited thereto. According to preferred embodiments of the present invention, the yeast may be selected from the group of the yeast consisting of *Yarrowia* sp., *Saccharomyces* sp., *Pichia* sp., and *Candida* sp., but the present invention is not limited thereto. According to other preferred embodiments of the present invention, the *Yarrowia* sp. yeast may be *Yarrowia lipolytica*, but the present invention is not limited thereto.

According to another aspect of the present invention, there is provided a method for producing a medium chain diol, which comprises (1) preparing a recombinant microorganism from which one or more genes selected from the group consisting of fatty alcohol dehydrogenase and fatty alcohol oxidase genes in an ω-oxidative metabolism pathway are deleted, a fatty aldehyde dehydrogenase gene is optionally deleted, and β-oxidative metabolism pathway-related genes are also deleted; and (2) treating the recombinant microorganism with a substrate to culture the recombinant microorganism.

According to an embodiment of the present invention, the substrate may be selected from the group consisting of a fatty acid-derived alcohol and alkane, but the present invention is not limited thereto. According to preferred embodiments of the present invention, each of the fatty acid-derived alcohol and alkane and the medium chain diol may have 5 to 30 carbon atoms, preferably 6 to 20 carbon atoms, and more preferably 8 to 16 carbon atoms, but the present invention is not limited thereto. According to other preferred embodiments of the present invention, the alkane may be dodecane, but the present invention is not limited thereto. According to still other preferred embodiments of the present invention, the medium chain diol may be 1,12-dodecanediol, but the present invention is not limited thereto.

Advantageous Effects

Because fatty alcohol dehydrogenase and/or fatty alcohol oxidase genes in an ω-oxidative metabolism pathway are deleted, a fatty aldehyde dehydrogenase gene is optionally deleted, and β-oxidative metabolism pathway-related genes are also deleted from a recombinant microorganism according to the present invention, the recombinant microorganism can produce medium chain diols with high yield by preventing further oxidation and β-oxidative metabolism of fatty alcohols.

DESCRIPTION OF DRAWINGS

FIG. 5 is a graph illustrating types of knock-out genes in the transformant microorganism according to the present invention.

FIG. 8 shows the GC/MS data showing that the medium chain diol is produced the alkane substrate in the Y4-20 strain according to the present invention.

BEST MODE

The present invention provides a recombinant microorganism from which one or more genes selected from the group consisting of fatty alcohol dehydrogenase and fatty alcohol oxidase genes in an ω-oxidative metabolism pathway are deleted, a fatty aldehyde dehydrogenase gene is optionally deleted, and β-oxidative metabolism pathway-related genes are also deleted.

Figure 1:
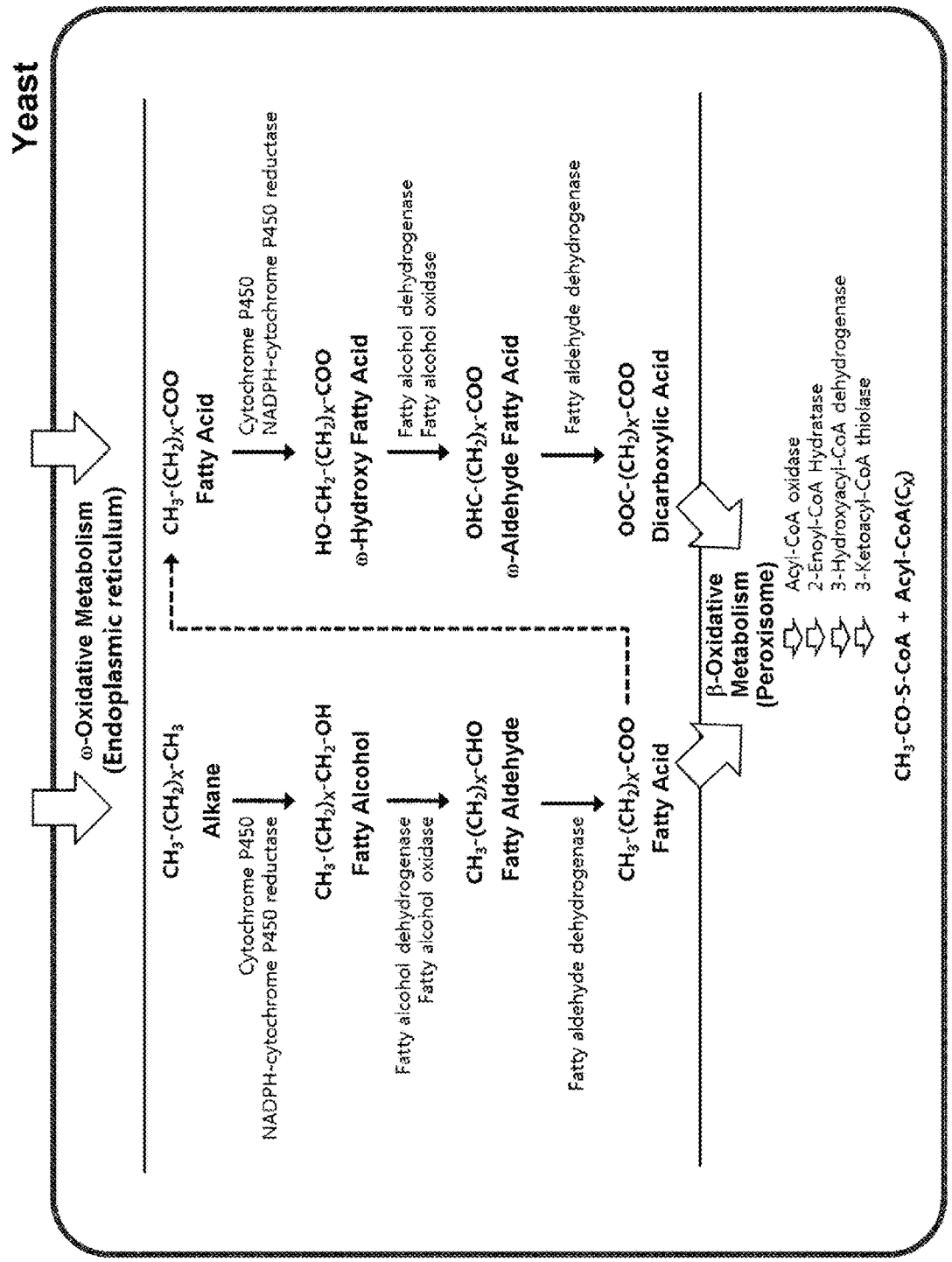
FIG. 1 is a diagram showing types of products and related enzymes associated with ω-oxidative and β-oxidative metabolism reactions.

In the present invention, the term "ω-oxidation" refers to a metabolic process in which the terminal methyl group of a fatty acid is oxidized to form dicarboxylic acid, and the term "β-oxidation" refers to a metabolic process in which a carbon atom at the β-position in a carboxyl group is oxidized to release acetyl-CoA, whereby fatty acids are gradually decomposed to form fatty acids whose number of carbon atoms is reduced by two. The concept of the ω- and β-oxidations and the enzymes involved in such metabolic processes are widely known to persons having ordinary skill in the field of biochemistry. For example, when a fatty acid is used as the substrate for ω-oxidation, an ω-hydroxy fatty acid is first produced by means of an action of cytochrome P450 and an NADPH-cytochrome P450 reductase. Then, the ω-hydroxy fatty acid is converted into ω-aldehyde fatty acid by an action of a fatty alcohol dehydrogenase and a fatty alcohol oxidase, and the ω-aldehyde fatty acid is converted into dicarboxylic acid by an action of a fatty aldehyde dehydrogenase. Also, for the β-oxidation, a fatty acid whose number of carbon atoms is reduced by two is produced by an acyl-CoA oxidase (see FIG. 1).

According to an embodiment of the present invention, the fatty alcohol dehydrogenase and fatty alcohol oxidase genes and the fatty aldehyde dehydrogenase gene that may be optionally deleted are preferably deleted from all homologous genes present in the corresponding microorganism, but a recombinant microorganism from which some of these genes are deleted may also be applied to the present invention, when necessary.

According to an embodiment of the present invention, the fatty alcohol dehydrogenase gene may be selected from the group consisting of ADH1, ADH2, ADH3, ADH4, ADH5, ADH6, ADH7, ADH8, and FADH genes, but the present invention is not limited thereto. According to preferred embodiments of the present invention, the ADH1, ADH2, ADH3, ADH4, ADH5, ADH6, ADH7, ADH8, and FADH genes may comprise base sequences set forth in SEQ ID NOs: 1 to 9, respectively, but the present invention is not limited thereto.

According to another embodiment of the present invention, the fatty alcohol oxidase gene may be an FAO gene, but the present invention is not limited thereto. According to preferred embodiments of the present invention, the FAO gene may comprise a base sequence set forth in SEQ ID NO: 10, but the present invention is not limited thereto.

According to still another embodiment of the present invention, the fatty aldehyde dehydrogenase gene may be selected from the group consisting of FALDH1, FALDH2, FALDH3, and FALDH4 genes, but the present invention is not limited thereto. The FALDH1, FALDH2, FALDH3, and FALDH4 genes may comprise base sequences set forth in SEQ ID NOs: 11 to 14, respectively, but the present invention is not limited thereto.

Figure 2:
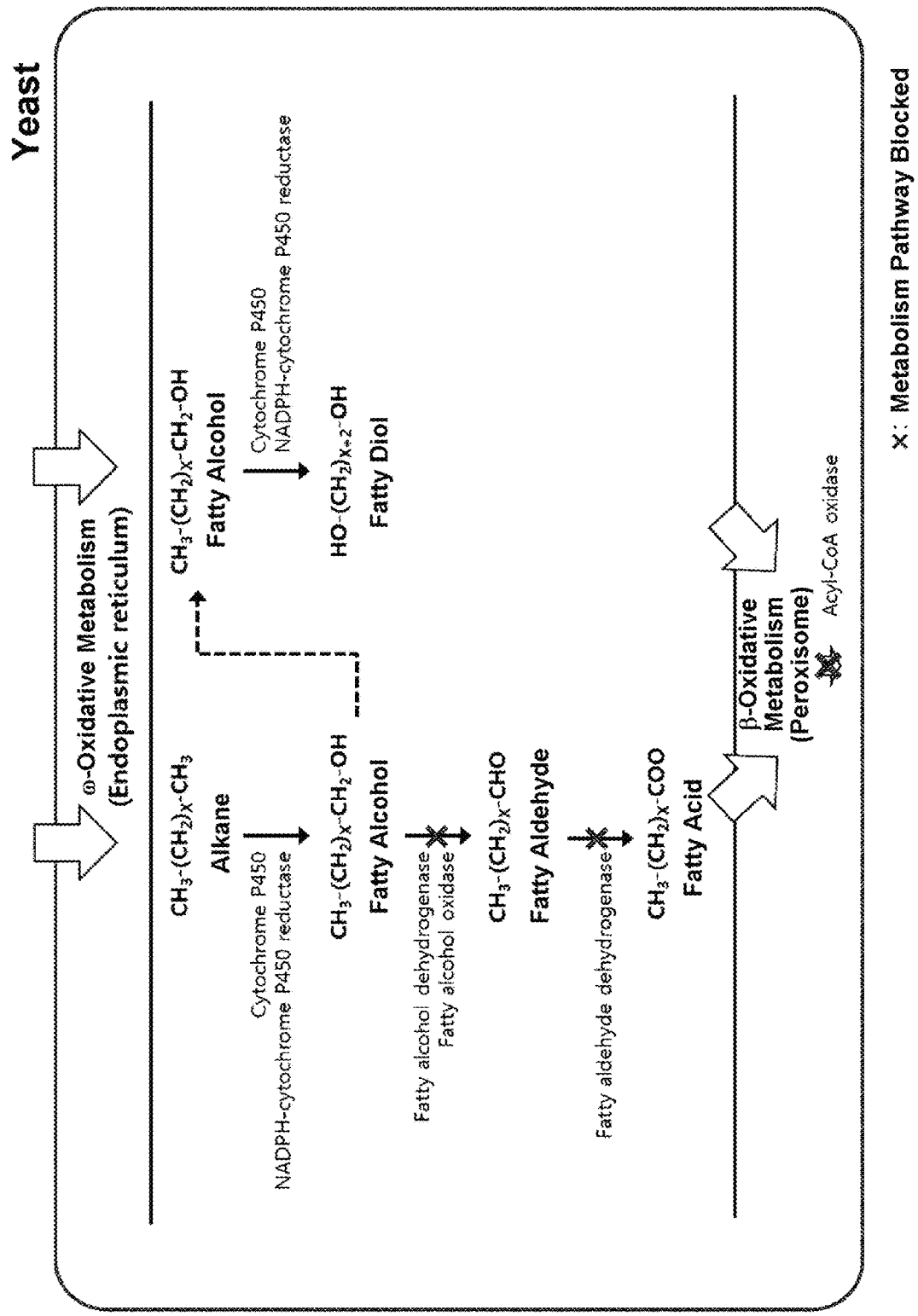
FIG. 2 is a diagram schematically showing a process of preparing a recombinant microorganism of the present invention from which fatty alcohol dehydrogenase, fatty alcohol oxidase and fatty aldehyde dehydrogenase genes associated with ω-oxidation and an acyl-CoA oxidase gene associated with β-oxidation are deleted.

According to an embodiment of the present invention, the β-oxidative metabolism pathway-related genes are preferably deleted from all homologous genes present in the corresponding microorganism, but a recombinant microorganism from which some of these genes are deleted may also be applied to the present invention, when necessary. The β-oxidative metabolism pathway-related genes preferably includes an acyl-CoA oxidase gene, and the acyl-CoA oxidase gene may be selected from the group consisting of ACO1, ACO2, ACO3, ACO4, ACO5, and ACO6 genes, but the present invention is not limited thereto (see FIG. 2). According to other preferred embodiments of the present invention, the ACO1, ACO2, ACO3, ACO4, ACO5, and ACO6 genes may comprise base sequences set forth in SEQ ID NOs: 15 to 20, respectively, but the present invention is not limited thereto.

In the present invention, the recombinant microorganism from which the genes selected from the fatty alcohol dehydrogenase gene, the fatty alcohol oxidase gene, the fatty aldehyde dehydrogenase gene, and the acyl-CoA oxidase gene are deleted may be prepared using conventional genetic recombinant technology known in the related art. In the present invention, the term "deletion" is used as a meaning generally encompassing a physical deletion of part or all of the corresponding gene, and also encompassing a situation in which a protein is not expressed from mRNA transcribed from the corresponding gene and a situation in which a protein expressed from the corresponding gene does not function. Examples of the genetic recombinant technology that may be used herein may include methods such as transformation, transduction, transfection, microinjection, electroporation, and the like, but the present invention is not limited thereto.

In the present invention, any microorganisms having both ω-oxidative and β-oxidative metabolism processes may be used without limitation. For example, eukaryotes including a yeast and prokaryotes including *Escherichia coli* may be used. According to an embodiment of the present invention, the yeast is preferably used as the microorganism. In this case, yeasts such as *Yarrowia* sp., *Saccharomyces* sp., *Pichia* sp., *Candida* sp., and the like may be used as the yeast without limitation. Among theses, *Yarrowia hpolytica*, *Candida tropicalis*, *Candida infanticola*, *Saccharomyces cerevisiae*, *Pichia alcoholophia*, or *Candida mycoderma* is preferably used. *Yarrowia lipolytica* is more preferably used.

As described above, in the case of the microorganism from which the fatty alcohol dehydrogenase and fatty alcohol oxidase genes and the β-oxidative metabolism pathway-related genes are deleted and the fatty aldehyde dehydrogenase gene is optionally deleted, when the alkane is supplied as the substrate, one of both terminals of the alkane is oxidized by an action of cytochrome P450 and an NADPH-cytochrome P450 reductase to form a primary alcohol. However, because the fatty alcohol dehydrogenase gene and the fatty alcohol oxidase gene are deleted, no further oxidation occurs anymore. Also, the primary alcohol thus formed is again used as a substrate so that the other terminal of the primary alcohol is oxidized by an action of the cytochrome P450 and the NADPH-cytochrome P450 reductase to form a diol as a secondary alcohol. When the alkane is used as the substrate as described above, the diol is formed through a two-step oxidation reaction, whereas the diol is formed through a one-step oxidation reaction when the alcohol other than the alkane is used as the substrate.

Also, the present invention provides a method for producing a medium chain diol, which comprises:

(1) preparing a recombinant microorganism from which one or more genes selected from the group consisting of fatty alcohol dehydrogenase and fatty alcohol oxidase genes in an ω-oxidative metabolism pathway are deleted, a fatty aldehyde dehydrogenase gene is optionally deleted, and β-oxidative metabolism pathway-related genes are also deleted; and (2) treating the recombinant microorganism with a substrate to culture the recombinant microorganism.

In the present invention, the recombinant microorganism, from which the fatty alcohol dehydrogenase and/or fatty alcohol oxidase genes in the ω-oxidative metabolism pathway are deleted, the fatty aldehyde dehydrogenase gene is optionally deleted, and the β-oxidative metabolism pathway-related genes are also deleted, may be used to produce medium chain diols with high yield by preventing additional oxidation and β-oxidative metabolism of fatty alcohols. The fatty alcohol dehydrogenase gene, the fatty alcohol oxidase gene, the fatty aldehyde dehydrogenase gene, and the β-oxidative metabolism pathway-related genes are preferably deleted from all homologous genes present in the corresponding microorganism, but a recombinant microorganism from which some of these genes are deleted may also be applied to the present invention, when necessary.

In the present invention, any microorganisms having both ω-oxidative and β-oxidative metabolism processes may be used without limitation. For example, eukaryotes including a yeast and prokaryotes including *Escherichia coli* may be used. According to an embodiment of the present invention, the yeast is preferably used as the microorganism. In this case, yeasts such as *Yarrowia* sp., *Saccharomyces* sp., *Pichia* sp., *Candida* sp., and the like may be used as the yeast without limitation. Among theses, *Yarrowia lipolytica*, *Saccharomyces cerevisiae*, *Candida tropicalis*, *Candida infanticola*, *Pichia alcoholophia*, or *Candida mycoderma* is preferably used. *Yarrowia lipolytica* is more preferably used.

In the present invention, the recombinant microorganism from which the genes selected from the fatty alcohol dehydrogenase gene, the fatty alcohol oxidase gene, the fatty aldehyde dehydrogenase gene, and the acyl-CoA oxidase gene are deleted may be prepared using conventional genetic recombinant technology known in the related art. In the present invention, the term "deletion" is used as a meaning generally encompassing a physical deletion of part or all of the corresponding gene, and also encompassing a situation in which a protein is not expressed from mRNA transcribed from the corresponding gene and a situation in which a protein expressed from the corresponding gene does not function.

In the present invention, the term "diol" generally refers to a compound that contains two hydroxyl groups (—OH groups), and the term "medium chain diol" is used as a meaning encompassing all diol compounds having 5 to 30 carbon atoms, preferably 6 to 20 carbon atoms, and more preferably 8 to 16 carbon atoms.

In the present invention, the substrate of step (2) may be selected from the group consisting of a fatty acid-derived alcohol and alkane, but the present invention is not limited thereto. According to an embodiment of the present invention, alcohols having 5 to 30 carbon atoms, preferably 6 to 20 carbon atoms, and more preferably 8 to 16 carbon atoms may be used as the fatty acid-derived alcohol, but the present invention is not limited thereto. According to another embodiment of the present invention, alkanes having 5 to 30 carbon atoms, preferably 6 to 20 carbon atoms, and more preferably 8 to 16 carbon atoms may be used as the alkane, but the present invention is not limited thereto. According to preferred embodiments of the present invention, the alkane may be dodecane, but the present invention is not limited thereto. According to other preferred embodiments of the present invention, the medium chain diol may be 1,12-dodecanediol, but the present invention is not limited thereto.

MODE FOR INVENTION

Hereinafter, the present invention will be described in further detail with reference to examples thereof.

However, it should be understood that the following examples are just preferred examples for the purpose of illustration only and is not intended to limit or define the scope of the invention.

Example 1: Construction of Knock-Out Cassette

Figure 3:
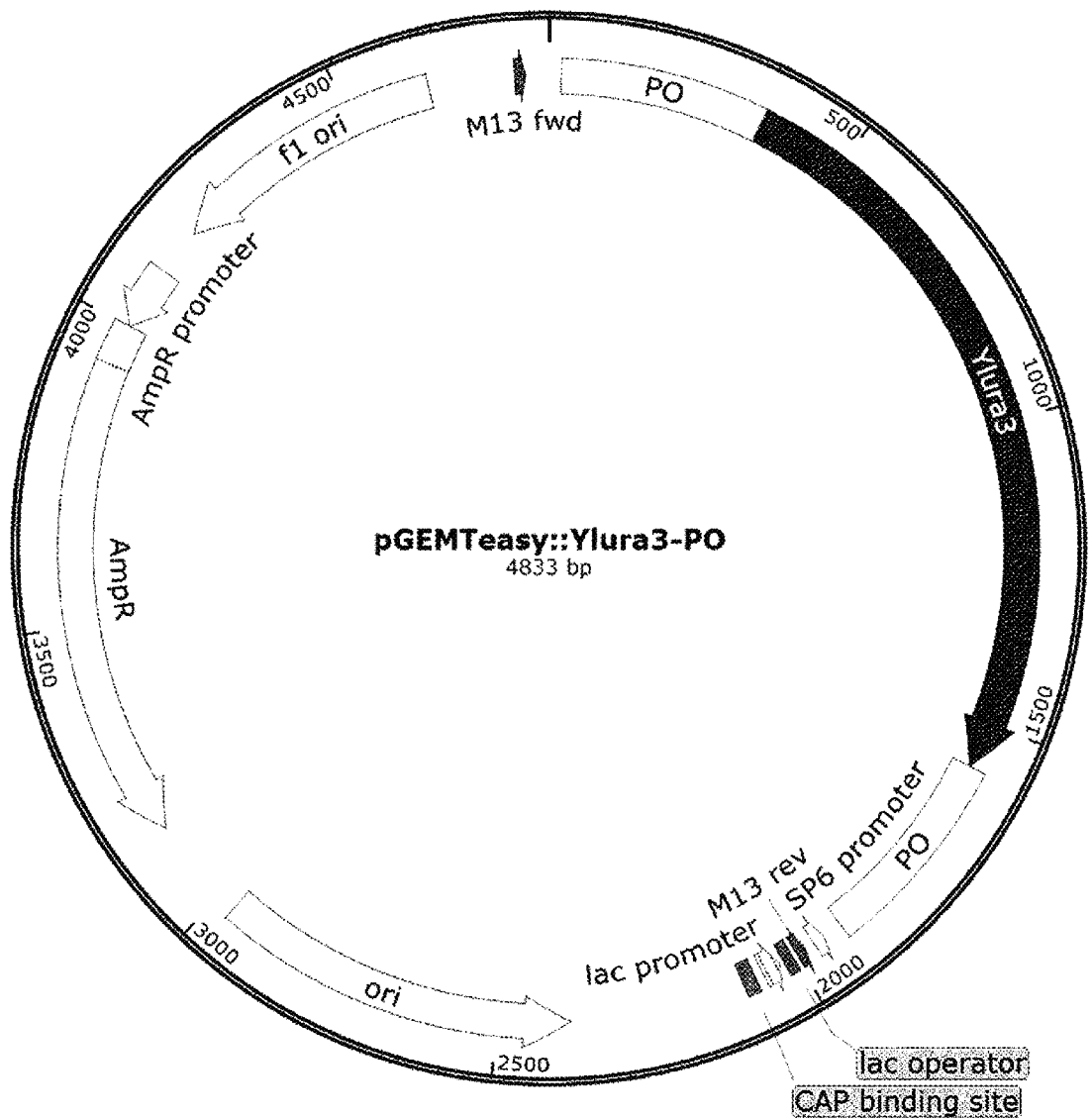
FIG. 3 is a diagram schematically showing a vector containing an ura3 gene to be used as a selective marker for gene knockout to modify a strain, and a pop-out region for deleting the ura3 gene after insertion of a knock-out cassette.

A vector containing an ura3 gene to be used as a selective marker for gene knockout to modify a strain, and a pop-out region for deleting the ura3 gene after insertion of a knock-out cassette was constructed (FIG. 3). A *Yarrowia*-derived gene was used as the ura3 gene, and the pop-out region used to modify a strain had a total of four sequences, and was referenced from two genes. Here, a *Bacillus*-derived glutamate-producing gene was used as one of the genes, and a gene associated with a *Salmonella*- or cloning vector pHUKH-derived His operon was used as the other one. The primers used to construct the pop-out vectors, and sequences thereof are listed in the following Table 1.

TABLE 1

Pop-out Vectors

| Names | | Base Sequences | SEQ ID NOs |
|---|---|---|---|
| HisG1 | BglII F | aattgggcccagatctcagaccggttcagacaggat | 22 |
| | EcoRI R | tctctgggcggaattcggaggtgcggatatgaggta | 23 |
| | NotI F | tgTTTCTCGgcggccgccagaccggttcagacaggat | 24 |
| | BamHI R | TCCAACGCGTGGATCCggaggtgcggatatgaggta | 25 |
| HisG2 | BglII F | aattgggcccagatctaacgctacctcgaccagaaa | 26 |
| | EcoRI R | tctctgggcggaattctcttctcgatcggcagtacc | 27 |
| | NotI F | tgTTTCTCGgcggccgcaacgctacctcgaccagaaa | 28 |
| | BamHI R | TCCAACGCGTGGATCCtcttctcgatcggcagtacc | 29 |
| glt2 | BglII F | aattgggcccagatctTCAGAACTTGCGCCGATAAA | 30 |
| | EcoRI R | tctctgggcggaattcCTTTGCCAGCTAGACCATAGAG | 31 |
| | NotI F | tgTTTCTCGgcggccgcTCAGAACTTGCGCCGATAAA | 32 |
| | BamHI R | TCCAACGCGTGGATCCCTTTGCCAGCTAGACCATAGAG | 33 |
| glt3 | BglII F | aattgggcccagatctATTGGCGGGTTCGTTACTT | 34 |
| | EcoRI R | tctctgggcggaattcCCTGGAAGAAGGCCGTATTATC | 35 |
| | NotI F | tgTTTCTCGgcggccgcATTGGCGGGTTCGTTACTT | 36 |
| | BamHI R | TCCAACGCGTGGATCCCCTGGAAGAAGGCCGTATTATC | 37 |

Figure 4:
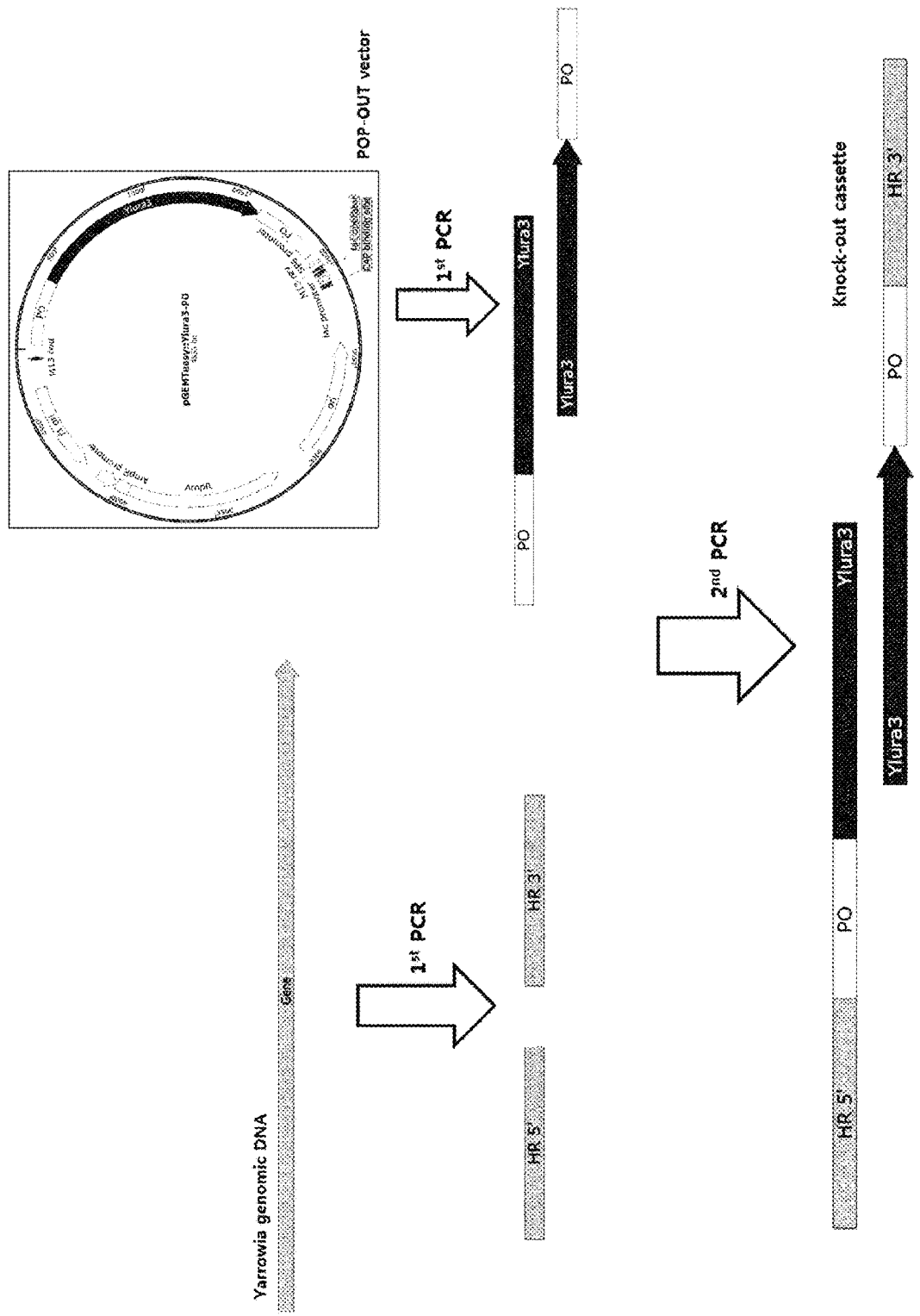
FIG. 4 is a schematic diagram showing a process of constructing a knock-out cassette used to prepare a transformant microorganism according to the present invention.

A knock-out cassette was constructed as shown in FIG. 4. First, PCR of a homologous region (HR) to be knocked out from the genomic DNA of *Yarrowia* sp., and PCR of two 5'- and 3'-terminal fragments from a pop-out vector were carried out. Thereafter, each of the 5' HR and 3' HR was subjected to alignment PCR ($2^{nd}$ PCR) with a PO-ura3 region to construct a knock-out cassette. The primers used to amplify the respective homologous regions, and sequences thereof are listed in Table 2.

TABLE 2

Gene Deletions

| Names | | Base Sequences | SEQ ID NOs |
|---|---|---|---|
| ACO1 | F1 | TTCCTCAATGGTGGAGAAGA | 38 |
| | R1 | TCTTTATCCTGTCTGAACCGGTCTGGTACCATAGTCCTTGCCATGC | 39 |
| | F2 | ATCGCTACCTCATATCCGCACCTCCCTTCTGTCCCCCGAGTTTCT | 40 |
| | R2 | AAGAAGGGCTTGAGAGTCG | 41 |
| ACO2 | F1 | CCCAACAACACTGGCAC | 42 |
| | R1 | TCTTTATCCTGTCTGAACCGGTCTGCTCCTCATCGTAGATGGC | 43 |
| | F2 | ATCGCTACCTCATATCCGCACCTCCgacaagacccgacaggc | 44 |
| | R2 | AGACCAGAGTCCTCTTCG | 45 |
| ACO3 | F1 | Accttcacagagccaccca | 46 |
| | R1 | ATGGCTCTCTGGGCGgtgttgggggtgttgatgatg | 47 |
| | F2 | TTGTTGTGTTTCTCGcaaggttctcatcgaggcctg | 48 |
| | R2 | Aggaaaggtcgaagagtgctct | 49 |

TABLE 2-continued

Gene Deletions

| Names | | Base Sequences | SEQ ID NOs |
|---|---|---|---|
| ACO4 | F1 | Actgcgagagcgatctg | 50 |
| | R1 | TCTTTATCCTGTCTGAACCGGTCTG TTCATGAGCATGTAGTTTCG | 51 |
| | F2 | ATCGCTACCTCATATCCGCACCTCC gaggacgacaaagccggag | 52 |
| | R2 | AGAGCAGAGTCCTCCTCAA | 53 |
| ACO5 | F1 | AACTTCCTCACAGGCAGCGAGC | 54 |
| | R1 | ATGGCTCTCTGGGCG GAGTAGAGAGTGGGAGTTGAGGTC | 55 |
| | F2 | ttgttgtgttttctcg ccccgtcaaggacgctgag | 56 |
| | R2 | ACAGTAAGGTGGGGCTTGACTC | 57 |
| ACO6 | F1 | AGTCCCTCAACACGTTTACCG | 58 |
| | R1 | TCTTTATCCTGTCTGAACCGGTCTG CCATTTAGTGGCAGCAACGTT | 59 |
| | F2 | ATCGCTACCTCATATCCGCACCTCC GAGCTCTGATCAACCGAACC | 60 |
| | R2 | AGGAAGGGTCTAATGACAGA | 61 |
| FALDH1 | F1 | AATCACTCCTCCTACGC | 62 |
| | R1 | TCTTTATCCTGTCTGAACCGGTCTG TGGTCTCGGGGACACCTC | 63 |
| | F2 | ATCGCTACCTCATATCCGCACCTCC CCATCATCAAGCCCCGAA | 64 |
| | R2 | ACCGACATAATCTGAGCAAT | 65 |
| FALDH2 | F1 | Accactaggtgagatcgag | 66 |
| | R1 | TCTTTATCCTGTCTGAACCGGTCTG CTCCGACACTACCGGAACG | 67 |
| | F2 | ATCGCTACCTCATATCCGCACCTCC CTTGCTCCCACAGTTGTT | 68 |
| | R2 | GATCACCCAGAACCATAGC | 69 |
| FALDH3 | F1 | GTGACCCCCACCACGTCAC | 70 |
| | R1 | TCTTTATCCTGTCTGAACCGGTCTG TTCTGACATTTTCAGCGCCAC | 71 |
| | F2 | ATCGCTACCTCATATCCGCACCTCC CCATTACGAGCGTTTGACGG | 72 |
| | R2 | CAGGGCTGGGGACCACC | 73 |
| FALDH4 | F1 | TACCGACTGGACCAGATTC | 74 |
| | R1 | TCTTTATCCTGTCTGAACCGGTCTG CGGCAGTGGCAATGATCTTAC | 75 |
| | F2 | ATCGCTACCTCATATCCGCACCTCC GACTCGATTCATCGCTCCTAC | 76 |
| | R2 | CAAATCTTTCGGAAGATTCGG | 77 |
| FAO1 | F1 | atcattgtcggtggaggaac | 78 |
| | R1 | ACGCCTTTCTGGTCGAGGTAGCGTTgcgtagtcgt aaggctggac | 79 |
| | F2 | attctggtactgccgatcgagaaga ccgtcatcggtgagattctt | 80 |
| | R2 | attcgaggtcggagatcctt | 81 |
| ADH1 | F1 | cccagaaggctgtcattttc | 82 |
| | R1 | ACGCCTTTCTGGTCGAGGTAGCGTTtcgcagttct tggggatatg | 83 |
| | F2 | attctggtactgccgatcgagaaga gccgacaaggagaagatgtg | 84 |
| | R2 | caatcttgccctcctccat | 85 |
| ADH2 | F1 | ccagaagggtgtcatcttcg | 86 |
| | R1 | ACGCCTTTCTGGTCGAGGTAGCGTTatcgcagttc ttgggaatgt | 87 |
| | F2 | attctggtactgccgatcgagaaga ccgacaaggagaagatgtgc | 88 |
| | R2 | caatcttgccctcctccata | 89 |
| ADH3 | F1 | agaaagccgtcatcttcgag | 90 |
| | R1 | ttgcacaagtaacgaacccgccaat tcacagttcttggggatgtg | 91 |
| | F2 | ggagataatacggccttcttccagg | 92 |

TABLE 2-continued

Gene Deletions

| Names | | Base Sequences | SEQ ID NOs |
|---|---|---|---|
| | | gctgacaaggagaagatgtgc | |
| | R2 | acttggagcagtccagaacg | 93 |
| ADH4 | F1 | gtcaaaacgtcgacgaacct | 94 |
| | R1 | AGGTATTTATCGGCGCAAGTTCTGA ggcttgaggtcaatgtcgat | 95 |
| | F2 | ctcctctatggtctagctggcaaag gacatggaggcccactctaa | 96 |
| | R2 | agtactcccaagcgtcctca | 97 |
| ADH5 | F1 | gagagccgcttttcaccac | 98 |
| | R1 | AGGTATTTATCGGCGCAAGTTCTGA agagcctggtaggcagtgag | 99 |
| | F2 | ctcctctatggtctagctggcaaag ttccaggacgtgatcaagga | 100 |
| | R2 | taaggatgatcttgccggtag | 101 |
| ADH6 | F1 | gacccagaaagccattgtgt | 102 |
| | R1 | AGGTATTTATCGGCGCAAGTTCTGA agccacctgagaaaggtctg | 103 |
| | F2 | ctcctctatggtctagctggcaaag caccgaggagaaggagaaga | 104 |
| | R2 | tccctcctccatcaaggtaa | 105 |
| ADH7 | F1 | gacgttcccaagacacaaaag | 106 |
| | R1 | AGGTATTTATCGGCGCAAGTTCTGA aggcgtactgctggaaagag | 107 |
| | F2 | ctcctctatggtctagctggcaaag acccacaccaaggagctg | 108 |
| | R2 | caacgacacgaccaacaatc | 109 |
| ADH8 | F1 | atcgcgccaacttgttaat | 110 |
| | R1 | AGGTATTTATCGGCGCAAGTTCTGA caccttctctcgtgggatgt | 111 |
| | F2 | ctcctctatggtctagctggcaaag tgtgttgagtctggcaaagc | 112 |
| | R2 | tcaagtccatggcatcaaac | 113 |
| FADH | F1 | ccgaaggaaagaccatcact | 114 |
| | R1 | ttgcacaagtaacgaacccgccaat agaaggaagagcagcccata | 115 |
| | F2 | ggagataatacggccttcttccagg gcttgggcttacaagtttgg | 116 |
| | R2 | tcggtgaaggcagagttgat | 117 |

The primers used to PCR-amplify the pop-out region and ura3 as two fragments are listed in Table 3.

TABLE 3

Pop-out Cassettes

| Names | | Base Sequences | SEQ ID NOs |
|---|---|---|---|
| HISG1 | F | cagaccggttcagacaggat | 118 |
| | R | ggaggtgcggatatgaggta | 119 |
| HISG2 | F | aacgctacctcgaccagaaa | 120 |
| | R | tcttctcgatcggcagtacc | 121 |
| glt2 | F | TCAGAACTTGCGCCGATAAA | 122 |
| | R | CTTTGCCAGCTAGACCATAGAG | 123 |
| glt3 | F | ATTGGCGGGTTCGTTACTT | 124 |
| | R | CCTGGAAGAAGGCCGTATTATC | 125 |
| Bipartite | Ulura3 cs 2B | atgccctcctacgaagctcgagc | 126 |
| | Ylura3F | ctcccaacgagaagctggcc | 127 |

The gene sequences used to modify the recombinant microorganism strain according to the present invention are listed in the sequence listing, and summarized in Table 4.

TABLE 4

| Genes | SEQ ID NOs |
|---|---|
| ADH1 | 1 |
| ADH2 | 2 |
| ADH3 | 3 |
| ADH4 | 4 |
| ADH5 | 5 |
| ADH6 | 6 |
| ADH7 | 7 |
| ADH8 | 8 |
| FADH | 9 |
| FAO1 | 10 |
| FALDH1 | 11 |
| FALDH2 | 12 |
| FALDH3 | 13 |
| FALDH4 | 14 |
| ACO1 | 15 |
| ACO2 | 16 |
| ACO3 | 17 |
| ACO4 | 18 |
| ACO5 | 19 |
| ACO6 | 20 |
| Ura3 | 21 |

Example 2: Construction of Knock-Out Strain

The knock-out cassette constructed in Example 1 was used to prepare a total of six knock-out strains from which some or all of fatty alcohol dehydrogenase, fatty alcohol oxidase and fatty aldehyde dehydrogenase genes and β-oxidative metabolism pathway-related genes present in a wild-type *Yarrowia* strain were deleted (FIG. 5). Specifically, a strain to be knocked out was plated on an YPD plate, and cultured at 30° C. for 16 to 24 hours. The cultured cells were scraped with a loop, put into 100 μL of a one-step buffer (45% PEG4000, 100 mM DTT, 0.1 L LiAc, 25 μg of single-strand carrier DNA), and vortexed. Thereafter, the knock-out cassette (1 ng or more) was added thereto, and the resulting mixture was vortexed again, and cultured at 39° C. for an hour. The cultured sample was loaded onto a selective medium (6.7 g/L of YNB without amino acids, and 20 g/L of glucose), and then cultured at 30° C. for 48 hours to screen a strain into which the constructed cassette was inserted. To check whether the cassettes were correctly inserted onto the genome of the screened strain, PCR was then performed using the primers included in the gene deletions listed in Table 2.

To insert another cassette, a pop-out process was performed on the strain into which the cassette was inserted. The strain screened from a selective medium was inoculated in 2 mL of an YPD medium, and cultured at 30° C. for 16 hours, and 200 μL of the culture broth was spread on a 5' FOA medium (6.7 g/L of YNB without amino acids, 20 g/L of glucose, 0.8 g/L of 5' FOA, 0.1 g/L of uracil, and 0.1 g/L of uridine), and then cultured at 30° C. for 48 hours. The strains grown on the 5' FOA medium were picked, and plated on an YPD plate and a UD plate. Then, the strains grown on the YPD plate were screened, and a PCR process was again performed using the primers listed in Table 2 to check whether the ura3 gene was deleted from the strains. A knock-out process was performed on other genes of the Ura3-deleted strains.

The aforementioned processes were repeatedly performed to prepare the recombinant microorganism strain of the present invention (Chen D C, Beckerich J M, Gaillardin C (1997) *Appl Microbiol Biotechnol* 48: 232-235).

Example 3: Culturing of Knock-Out Strain

A day earlier, the strain to be cultured and tested was inoculated in 2 mL of an YPD medium (Bacto Laboratories, 10 g/L of Yeast extract, 20 g/L of peptone, and 20 g/L of glucose), and grown at 30° C. and 200 rpm for a day. 2 mL of a growth medium (pH 6.0) having the compositions listed in Table 5 was put into a 24-well plate, and a pre-cultured culture broth was inoculated at 1%. Thereafter, the strains were cultured at 30° C. and 450 rpm for a day in a plate stirrer. The strains cultured for a day were inoculated at a volume of 900 μL in a new plate containing 900 μL of a conversion medium (pH 7.6) listed in Table 6, and 200 μL of a substrate was added thereto at the same time. The resulting mixture was cultured at 30° C. and 450 rpm for a day. In this case, 10 g/L of dodecane dissolved in DMSO was used as the substrate.

TABLE 5

Growth Medium (pH 6.0)

| Components | Concentration (g/L) |
|---|---|
| Glucose | 50 |
| YNB w/o amino acids | 6.7 |
| Yeast extract | 10 |
| $(NH_4)_2SO_4$ | 5 |
| Uracil | 0.05 |
| 0.1M phosphate buffer | |

Preparation of 0.1M potassium phosphate buffer at 25° C.

| pH | Volume (mL) of 1M $K_2HPO_4$ | Volume (mL) of 1M $KH_2PO_4$ |
|---|---|---|
| 6.0 | 13.2 | 86.8 |

TABLE 6

Conversion Medium (pH 7.6)

| Components | Concentration (g/L) |
|---|---|
| Glucose | 30 |
| YNB w/o amino acids | 6.7 |
| Yeast extract | 3 |
| $(NH_4)_2SO_4$ | 15 |
| Uracil | 0.05 |
| L-alanine | 10 |
| 0.1M phosphate buffer | |

Preparation of 0.1M potassium phosphate buffer at 25° C.

| pH | Volume (mL) of 1M $K_2HPO_4$ | Volume (mL) of 1M $KH_2PO_4$ |
|---|---|---|
| 7.6 | 86.6 | 13.4 |

Figure 6:
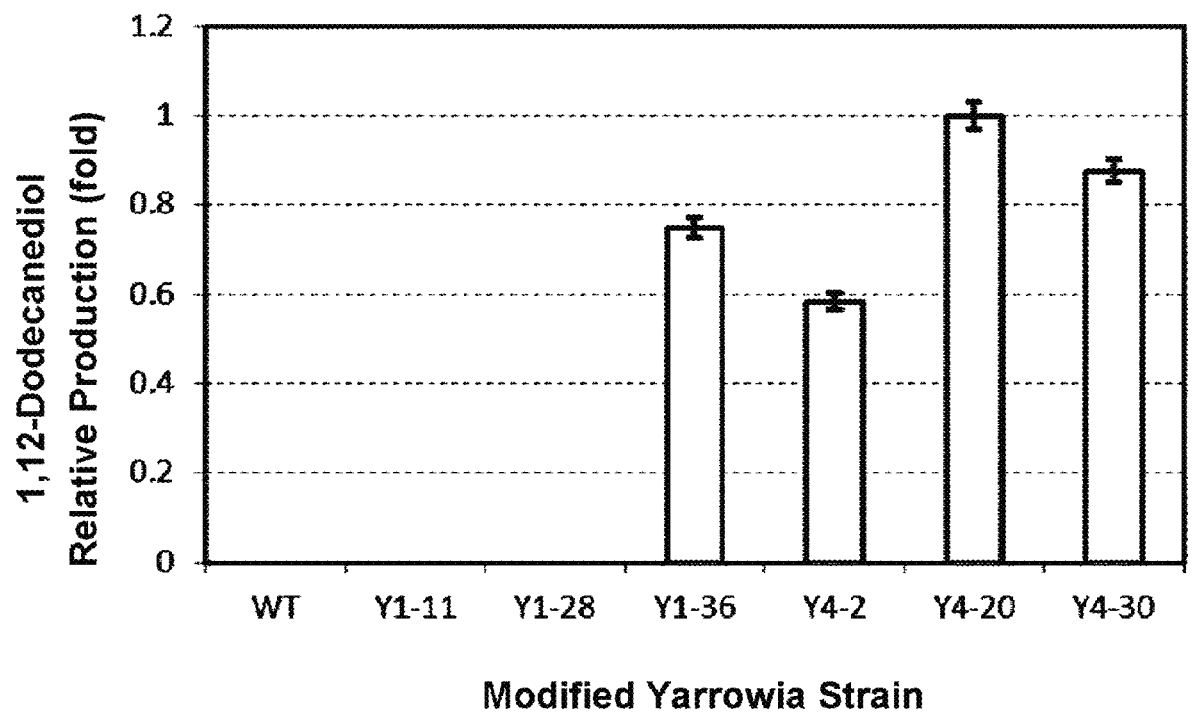
FIG. 6 is a graph illustrating an amount of a medium chain diol produced from the alkane substrate, using the transformant microorganism according to the present invention.
Figure 7:
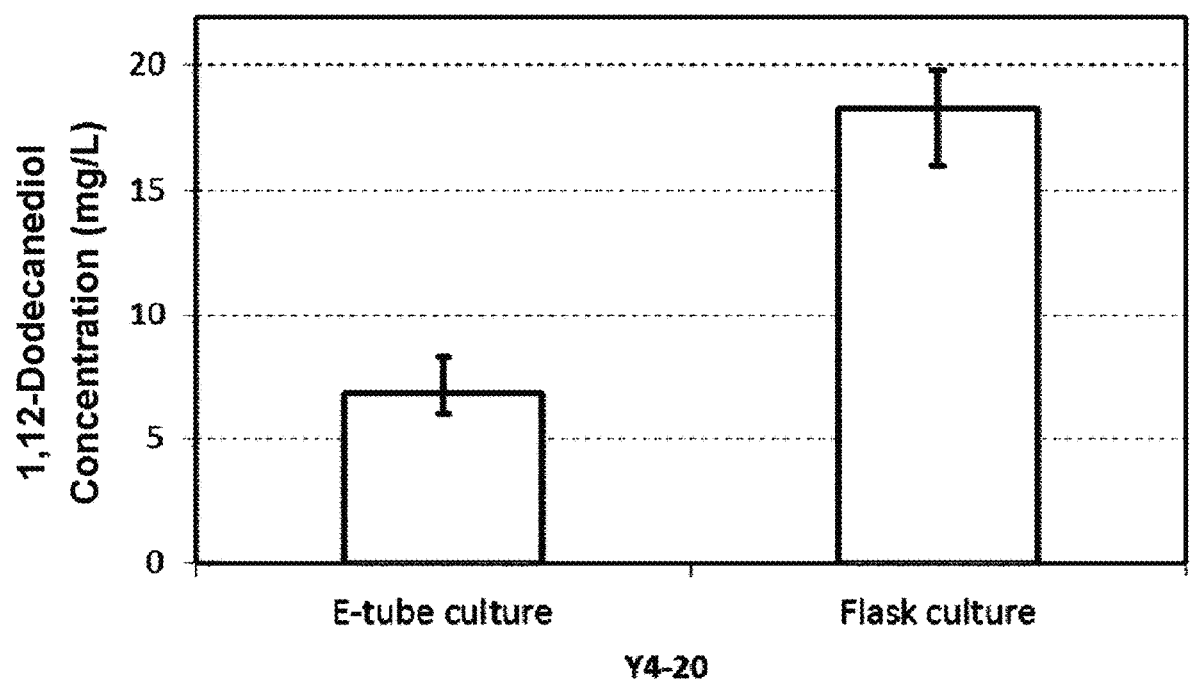
FIG. 7 is a graph illustrating an amount of the medium chain diol produced from the alkane substrate, when an Y4-20 strain of the present invention is cultured in a flask.

As a result, it was revealed that the Y1-28 and Y1-36 strains in which only the β-oxidative metabolism pathway-related genes and the fatty aldehyde dehydrogenase gene were knocked out did not produce 1,12-dodecanediol from dodecane serving as the substrate, but all the Y1-36 strain in which the fatty alcohol oxidase gene was further knocked out, and the Y4-2, Y4-20 and Y4-30 strains in which the fatty alcohol oxidase gene and the fatty alcohol dehydrogenase gene were further knocked out exhibited an excellent ability to synthesize 1,12-dodecanediol (FIG. 6). Also, it was revealed that the Y4-20 strain exhibited an ability to synthesize approximately 18 mg/L of 1,12-dodecanediol when cultured in the flask (FIG. 7). In the following experiment, a sample analysis test was performed using the Y4-20 strain.

Example 4: Sample Analysis 1 mL of 1 N sodium hydroxide and 10 mL of chloroform were added to 10 mL of a culture broth of the Y4-20 strain which had been proven to have the most excellent ability to synthesize 1,12-dodecanediol in Example 3. Thereafter, the resulting mixture was thoroughly vortexed, extracted, and then centrifuged at 10,000 rpm for 10 minutes. Then, only a chloroform layer was separated, concentrated 10-fold, and then subjected to a GC/MS assay under the following analytical conditions.

Analytical Conditions
① Equipment: Agilent 5975 MSD®
② Column: HP-5MS
③ Temperature: Oven (150° C. to 230° C.)
④ Carrier gas: He
⑤ Flow rate: 1 mL/min.

As a result, it was confirmed that the recombinant Y4-20 strain of the present invention was able to synthesize 1,12-dodecanediol from dodecane serving as a substrate (FIG. 8).

The invention claimed is:

1. A recombinant microorganism from which all of fatty alcohol dehydrogenase genes, fatty alcohol oxidase genes in an ω-oxidative metabolism pathway and fatty aldehyde dehydrogenase gene are completely deleted, and β-oxidative metabolism pathway-related genes are also deleted, wherein the fatty alcohol dehydrogenase genes are ADH1, ADH2, ADH3, ADH4, ADH5, ADH6, ADH7, ADH8, and FADH genes, and the recombinant microorganism is *Yarrowia lipolytica*.

2. The recombinant microorganism of claim 1, wherein each of the ADH1, ADH2, ADH3, ADH4, ADH5, ADH6, ADH7, ADH8 and FADH genes comprises base sequences set forth in SEQ ID NOs: 1 to 9, respectively.

3. The recombinant microorganism of claim 1, wherein the fatty alcohol oxidase gene is an FAO gene.

4. The recombinant microorganism of claim 3, wherein the FAO gene comprises a base sequence set forth in SEQ ID NO: 10.

5. The recombinant microorganism of claim 1, wherein the fatty aldehyde dehydrogenase genes are FALDH1, FALDH2, FALDH3, and FALDH4 genes.

6. The recombinant microorganism of claim 5, wherein each of the FALDH1, FALDH2, FALDH3, and FALDH4 genes comprises base sequences set forth in SEQ ID NOs: 11 to 14, respectively.

7. The recombinant microorganism of claim 1, wherein the β-oxidative metabolism pathway-related gene is an acyl-CoA oxidase gene.

8. The recombinant microorganism of claim 7, wherein the acyl-CoA oxidase genes are ACO1, ACO2, ACO3, ACO4, ACO5, and ACO6 genes.

9. The recombinant microorganism of claim 8, wherein each of the ACO1, ACO2, ACO3, ACO4, ACO5, and ACO6 genes comprises base sequences set forth in SEQ ID NOs: 15 to 20, respectively.

10. A method for producing a medium chain diol, comprising:
(1) preparing the recombinant microorganism according to claims 1; and
(2) treating the recombinant microorganism with a substrate to culture the recombinant microorganism.

11. The method of claim 10, wherein the substrate is selected from the group consisting of a fatty acid-derived alcohol and alkane.

12. The method of claim 11, wherein the fatty acid-derived alcohol is an alcohol having 5 to 30 carbon atoms.

13. The method of claim 11, wherein the alkane is an alkane having 5 to 30 carbon atoms.

14. The method of claim 12, wherein the medium chain diol is a diol compound having 5 to 30 carbon atoms.

* * * * *

SEQUENCE LISTING

```
<160> NUMBER OF SEQ ID NOS: 127

<210> SEQ ID NO 1
<211> LENGTH: 1050
<212> TYPE: DNA
<213> ORGANISM: Yarrowia lipolytica
<220> FEATURE:
<221> NAME/KEY: gene
<222> LOCATION: (1)..(1050)
<223> OTHER INFORMATION: ADH1 gene

<400> SEQUENCE: 1
atgaccacca tccccaagac ccagaaggct gtcattttcg agacctccgg cggtcctctc      60
atgtacaagg acgtgcctgt gcctgttcct gccgacgacg agattctcgt caacgtcaag     120
ttttccggag tgtgccacac tgacctccat gcctggaagg gcgactggcc tcttgacacc     180
aaacttcctc tcattggcgg ccacgagggc gccggagttg tcgtggccaa gggcaagaac     240
gtgaccacct tcgaaatcgg cgactacgcc ggtatcaagt ggattaacaa ggcctgttac     300
acctgtgagt tctgccaggt gtctgccgag cccaactgtc ctaaagctac catgtcggga     360
tacacccacg acggctcgtt ccagcagtac gccactgcca acgctgtcca ggcagcccat     420
atccccaaga actgcgacct cgcccagatt gctcccattc tctgcgccgg catcaccgtc     480
tacaaggctc ttaagaccgc tggcctcaag gctggtgagt gggccgccgt taccggagct     540
ggaggaggcc tcggttctct ggccgtccag tacgctaagg ccatgggcta ccgagtgctg     600
gccattgaca ccggcgccga caaggagaag atgtgcaagg agctcggcgc cgaggtcttc     660
atcgactttg ctaagtccaa ggatctggtc aaggacgtcc aggatgccac caagggcgga     720
ccccacgccg ttatcaacgt gtctgtctcc gagtttgccg tcaaccagtc cgtcgagtac     780
gtgcgaactc tgggcaccgt ggttctggtc ggcctgcccg ctggagctgt ctgcaagtcg     840
cccatcttcc agcaagtggc tcgatccatt cagatcaagg gttcctatgt tggcaaccga     900
gccgactcgc aggaggccat tgaattcttc gcccggggcc ttgtcaagtc tcccattatt     960
attgtgggtc tttcccagct ggagtccgtc tacaagctga tggaggaggg caagattgcc    1020
ggcagatacg ttctggacac ttacaagtaa                                      1050

<210> SEQ ID NO 2
<211> LENGTH: 1056
<212> TYPE: DNA
<213> ORGANISM: Yarrowia lipolytica
<220> FEATURE:
<221> NAME/KEY: gene
<222> LOCATION: (1)..(1056)
<223> OTHER INFORMATION: ADH2 gene

<400> SEQUENCE: 2
atgtctgctc ccgtcatccc caagacccag aagggtgtca tcttcgagac ctccggcggt       60
```

```
cctctcatgt acaaggacat ccccgtgcct gtgcctgccg acgacgagat tctggtcaac    120
gtcaagttct ccggagtctg ccacacggat ctgcacgcct ggaagggcga ctggcctctg    180
gacaccaagc ttcctctggt cggaggccac gagggtgccg agtggttgt tgccaagggt    240 aagaacgttg acacgtttga gattggcgac tatgccggca tcaagtggat caacaaggcc    300
tgctacacct gcgagttctg ccaggtggcc gccgagccca actgtcccaa cgctaccatg    360
tctggataca cccacgacgg ctcttttccag cagtacgcca ccgccaacgc cgtgcaggcc    420
gcgcacattc caagaactg cgatctcgcc gagattgccc ccattctgtg cgccggaatc    480
accgtctaca aggctctcaa gactgccgcc atcctcgctg ccagtgggt tgccgttact    540 ggtgctggag gaggactcgg aacacttgct gtccagtacg ccaaggccat gggctaccga    600
gtgctggcca ttgacactgg cgccgacaag gagaagatgt gcaaggacct tggtgccgag    660
gttttcatcg actttgccaa gaccaaggac ctcgtcaagg acgtccagga ggccaccaag    720
ggcggacccc acgccgtcat caatgtgtct gtctccgagt ttgcagtcaa ccagtccatt    780
gagtacgtgc gaaccctggg aaccgttgtt ttggtcggtc tgcccgccgg cgccgtctgc    840
aagtctccca tcttccagca ggtggctcga tctatccaga tcaagggctc ttacgttgga    900
aaccgagccg actcccagga ggccattgag ttcttctccc gaggtctcgt caagtcgccc    960
atcatcatca tcggtctgtc cgagctggaa aaggtctaca agcttatgga ggagggcaag   1020
attgccggcc gatacgttct ggacacctcc aagtaa                              1056
```

<210> SEQ ID NO 3
<211> LENGTH: 1050
<212> TYPE: DNA
<213> ORGANISM: Yarrowia lipolytica
<220> FEATURE:
<221> NAME/KEY: gene
<222> LOCATION: (1)..(1050)
<223> OTHER INFORMATION: ADH3 gene

<400> SEQUENCE: 3

```
atgaccacca tccccaagac ccagaaagcc gtcatcttcg agacctccgg cggccccctc     60
atgtacaagg acgtgcctgt gcccgtgcct gccgacgacg agattctggt caacgtcaag    120
tactccggcg tgtgccacac ggacctgcac gcctggaagg gcgactggcc cctggacacc    180
aagctccccc tgattggcgg ccacgagggc gccggcgtgg ttgttgccaa gggcaagaac    240
gtgaccacct ttgagattgg cgactacgcc ggtatcaagt ggatcaacaa ggcctgctac    300
acctgcgagt tctgccaggt ggcggccgag cccaactgcc caaggccac catgtccgga    360 tacacccacg acggctcttt ccagcagtac gccaccgcca acgctgtcca ggccgcccac    420
atccccaaga actgtgacct cgcccaggtt gccccattc tctgcgccgg tatcaccgtc    480
tacaaggctc tcaagaccgc tggcctcaag gctggtgagt gggccgccgt gaccggagct    540
ggaggaggcc tcggctctct ggccgtccag tacgccaagg ccatgggcta ccgagtgctg    600
gccattgaca ctggcgctga caaggagaag atgtgcaagg agctcggcgc cgaggtcttc    660
atcgactttg ccaagtccaa ggatctggtc aaggacgtcc aggaggccac caagggcgga    720
ccccacgccg tcatcaacgt gtctgtctcc gagtttgccg tcaaccagtc tgttgagtac    780
gtgcgaaccc tgggaaccgt tgttctggtc ggtctgcccg ccggtgccgt ctgcaagtcg    840
cccatcttcc agcaggttgc tcgatctatt cagatcaagg gctcttacgt cggaaaccga    900
gccgactccc aggaggccat tgagttcttt gcccgaggac tggtcaagtc ccccatcatt    960
```

```
attgttggtc tctccgagct cgaatccgtc tacaagctca tggaggaggg caagattgcc    1020
ggtcgatacg ttctggactg ctccaagtaa                                    1050

<210> SEQ ID NO 4
<211> LENGTH: 1479
<212> TYPE: DNA
<213> ORGANISM: Yarrowia lipolytica
<220> FEATURE:
<221> NAME/KEY: gene
<222> LOCATION: (1)..(1479)
<223> OTHER INFORMATION: ADH4 gene

<400> SEQUENCE: 4
atggtcaaaa cgtcgacgaa ccttgcacga aacgtgctgc gaaccatcca ggccaaccct      60
cctcccggcc tcgaggtaaa tggcatcacc tcacacaact tcggagccta ccagcgggct     120 ttcacccca tggtgatgca gggagccgga cacagaaact acgccagtga tcacaaggag      180
acggagtacg cgttccagat ggccgcttcc aacatccgat acggccccgg cgtgacggca     240
gaggtgggct acgacttcaa gaacatgcga atcgaccggg tggctgtctt caccgacaag     300
aacctgctca taccccgc cgtcaaaacc gcactgcagt cgctcgacaa gtgtggaatc       360
aaatacgacc tttattcgga cgtgtgcgtt gagcccaaag agccctctgt gctcgacgcc    420
attgcctggg acgagctaa gcagcccaag gcctaccttg ccattggagg aggctctgtc     480
atggacactg ccaagatggc caacctgtac cagtgcttcc ccgacgctga gctgcttgat    540
ttcgtcaacg cccccattgg aaaggctcag cccatcgaca ttgacctcaa gcctctgatt    600
gccgtcccca ccactgccgg caccggatcc gagaccactg gaactgccat cttcgatctc    660
gtttcccgaa aggccaagac cggtattgct aaccgtgctc tgaagcccct gcttggaatt    720
gtcgatcctc tcaactctgc caccatgccc gagcaggtta aggccgcttc cggcctcgat    780
gtcctatgtc actctcttga gtcctacact gccatcccct accagcagcg aaccccccgt    840
cccagcaacc caacatgcg acctgcctac caaggatcca accccattgc tgatattttc    900
tctctcgagg gtctgcgtct ggccattgag taccttcctc gatcttgtgc cgaccccgaa    960
gacatggagg cccactctaa catgcttctt ggatctactc ttgccggtgt gggttttgga   1020
aacgccggtg ttcacatctg ccacggtctc tcttacccca tctctggaat gaacacctcc   1080
tactaccacc ccgactacca cactgaccat cctctggttc cccacggtat ctccgttgca   1140
gttactgctc cttctgtctt caagtttact gctcccagcg accccgagcg acatctcaag   1200
gccgcctctc tgtttggcgt tgatgtttcc aacgtcaagc gagagtctgc cggagaggtg   1260
cttgctgagg ccatccaaga gttcatgttc actaagctca agcaccaacc ccggggtgtc   1320
tctgctcttg gttacaagcg aagcgacatt tctgctctcg ttgacggtgc cgttcctcaa   1380
cgacgagttc ttgatctcgc ccccggtatc cacggtgttg aggaggccga ggtccgagag   1440
gcccttacct ctattcttga ggacgcttgg gagtactaa                           1479

<210> SEQ ID NO 5
<211> LENGTH: 1041
<212> TYPE: DNA
<213> ORGANISM: Yarrowia lipolytica
<220> FEATURE:
<221> NAME/KEY: gene
<222> LOCATION: (1)..(1041)
<223> OTHER INFORMATION: ADH5 gene

<400> SEQUENCE: 5
atgagagccg ctttcaccac cgcgtacggc ggtcccgaca agatcgagta ctccgattct     60
```

```
ctgcccaagg tgaagcttgg aggtgacgac cacgtgctca tccgagttgc cgacgcctcc      120
atcaacccca ttgatgggct gcgaaaccga ggaatgctgc gtattctcat gtgtgacgac      180
catccccacg tctttggata cgacgtcgga ggcttcgtcg aagaggtcgg ctccaagtgc      240
accaacctca aggttggcga ccgagtctac ggccgaattg cgagtctca gagcggcacc       300 ctcgccggct acgttctgc ccaggagagc gtcattgccg tggctcctac taacctgcct       360
ctgagcgaga ctgctggtgt gccttttggtt ggtctcactg cctaccaggc tctgagagcg     420
ggcgatgtgc agcctggaca gcgagtcttc atctccaagg cgctggagg agttggaacc      480 atcgctatcc agctcgccaa gcacgtcttt ggagcttatg tcattactac tggttcggac      540
cacaaggccg agcttctcaa agagcttgga gctgacgagg tcatcaacta ccgaaaggaa     600
aagttccagg acgtgatcaa ggagccagtc gactttgcct ttgacgtttc cgacgagcct     660
gccgcacatg caaagatcac caagaagaac ggattcgtgg cggctctgcg aggagctcct    720
tctcccgcta ctgccaagaa gattctggcc caccctcctg gattcctcat gaacaacgtt     780
ctgcgagccg ctaactttgc aacctcccga actgcctggt ggtacggagt ccgatacgag   840
gccatctact gcgttccttc tgctaaggat ctggacactc tgcgaggcta ccttgaaaag    900
ggtactatca agcccatcgt tgactgcact tatgacctca aggatgccaa gctagcaatg   960
gagaagcttg agagtggacg agctaccggc aagatcatcc ttagtgtgga tgatactctt   1020
gataaggagt tcaagcagta a                                                 1041

<210> SEQ ID NO 6
<211> LENGTH: 1047
<212> TYPE: DNA
<213> ORGANISM: Yarrowia lipolytica
<220> FEATURE:
<221> NAME/KEY: gene
<222> LOCATION: (1)..(1047)
<223> OTHER INFORMATION: ADH6 gene

<400> SEQUENCE: 6
atgacaatcc ccaagaccca gaaagccatt gtgttcgaaa cctctggagg tccccctggag     60 tacaaggacg tgcctgtgcc cgtgcccggc gaccatcaga ttctcgtcaa cgtcaagtac    120
tcgggagttt gccactctga cctccacgcc tggatgggag actggcctct acccaccaag    180
ctccctctta tcggcggcca cgaaggagcc ggcgtcgtgg tggccaaggg aaaaaacgtg   240
accacgttcg aaattggaga ctacgccgga atcaagtgga tcaaccaggc gtgctacacg   300
tgcgagttct gccaggaggc ctacgagccc aactgtccca ggcccagat tcgggatac      360 acaatggacg gaaccttcca gcagtatgca cttgcagatg ctgtgcaggc agcccacatt    420
ccccagggca cagaccttc tcaggtggct cctattctgt gtgccggagt gactgtttac     480
aaggccatca gacctctgg acgaaaggca ggagaatggt tggccgtgac aggtgcagga   540
ggaggactcg gatcgctggc ggtgcagtac gccaaggcca tgggtttccg agtgctggcc    600
atcgacacca ccgaggagaa ggagaagatg tgtctggaac tgggagcaga ggtctttgtg   660
gactttgcca agactgacaa tctggtggca cgagttcagg agattactgg aggtggccct    720
catggagtca tcaacgtttc tgtgtccgag tttgccatca accagtctct cgagtacgtt    780
cggtccgttg aactgttgt tctggtgggt ctgcctgctg gagctgtgtg caagtcgccc    840
atcttctcgc aggtggcccg ggctattacc atcaagggct ctcctgtggg taaccgagcc    900
gacacccagg aggctctgtc attctttacc cgaggattgg ttcactcgcc tattcatgtg   960
```

```
gtcggactgt ctgagctgca gaaggtgttt accttgatgg aggagggaaa gattgcgggt      1020
cggtatgttg tcgataccag caagtaa                                         1047

<210> SEQ ID NO 7
<211> LENGTH: 1065
<212> TYPE: DNA
<213> ORGANISM: Yarrowia lipolytica
<220> FEATURE:
<221> NAME/KEY: gene
<222> LOCATION: (1)..(1065)
<223> OTHER INFORMATION: ADH7 gene

<400> SEQUENCE: 7
atgagcgacg ttcccaagac acaaaaggcc gtcgttttcg aggaagtcaa cggacctttg        60
atgtacaagg acattcccgt ccccactccc gccaaggacg agctgctcgt caaggtgcag       120
tattccggtg tctgccactc ggatctgtcc atctggaagg gtgattgggc acagcagctg       180
cggttcagcc ccaagatgcc gctggtcggc ggtcatgagg agcaggaga ggttgtgggc        240 atgggcgatc aggtgaccgg atggcaggtc ggagaccgaa ccggagtcaa gtttatttct       300
ggctcttgtc tcacttgcga gcactgttct gctggctggg accagcactg cgtagccccc       360
ggcgtgtcag gtctgctcaa agacggctct ttccagcagt acgcctgcgt gaaggccgcc       420
accgcacccc gaatcccga ttcttgcgat ctggctggtg ttgcacccgt tctgtgtgca        480
ggcatcaccg cctacactgc cctcaagaac tctggtctca aggccggtga gtgggtggtg       540
atcaccggag ctggaggagg actcggatcc tacgccgtcc agtacgccaa gtgcatgggt       600
ttccgtgtga ttgccattga cactggagac gacaaggaga cccacaccaa ggagctggga       660
gccgaggtgt ttattgactt tgccaagagt ggtgctggca tgattgctga gattcacaag       720
ctcaccggag gtgcgcccca cgccgtggtc aactttgctg tgcaggacgc ggctgtcgag       780
gctgccactc tgtacgtgcg aacccgaggc actctggttc tgtgtgctct gccacccaac       840
ggtaccgtca agagtcacat tctcaaccac gtgggtcgag gactcaccat caagggcagt       900
tatgtgggta taagctgga tactcaggaa gccattgact tctatgcacg gggtctcgtc       960
aagaccaagt accgtctcgg cgagctgagc aagctcgagg agtattacca gcagatgctt      1020
gatggtaaga ttgttggtcg tgtcgttgtt gataacagca agtag                     1065

<210> SEQ ID NO 8
<211> LENGTH: 1275
<212> TYPE: DNA
<213> ORGANISM: Yarrowia lipolytica
<220> FEATURE:
<221> NAME/KEY: gene
<222> LOCATION: (1)..(1275)
<223> OTHER INFORMATION: ADH8 gene

<400> SEQUENCE: 8
atggtattga tcgaatcagg gtatgattat ggctatatac gtcttttcag aatcgcgcca        60
acttgtttaa ttgaggaatt aaaggccccc ttcttctcgt tccccacctt tgaacgaaca       120
cactatccaa ccctaactta aagcgaaaac cgatctacac aacacatcac ttcctgcgct       180
tttaccacaa gtcgtcgaca tctccttac cagcaattac actctctcga catgtctctg        240
ccactcaccg ataaatcttt caagcgtctg ggcaactctg gcctcaaggt gtcctccatc       300
attgtgggat gtatgtcgtt tggttctagc aactgggctc cttgggtcat tggagacgaa       360
gagcggtccc tggagctgct gaaggctgcc tacgaccgag gtttgcgaac gttcgacacc       420
gcctccacct actccaacgg tctctccgag gtgctactgg gcaagtttct gcgaaagtac       480
```

| | | |
|---|---|---|
| aacatcccac gagagaaggt ggtcattatg accaaggtgt tcttccccgt ggccgaggag | 540 | |
| ggactccacg gagagaccat tctcggcggt cgatcggagg aggagatgct ggagttcacc | 600 | |
| aaccgaatcg gactgtctcg aaagaacatt attgcctcgg tggacgactg ctgtgaacga | 660 | |
| ctcggcactt acattgatct gctgcagatc catcgactcg acgacgagtg tccctacgag | 720 | |
| gagatcatga aggccctgca tgactgtgtt gagtctggca agcccgcta cctaggagcc | 780 | |
| tcttccatgc gagccgtgga gtttgtggag ctgcagaacg tggctgagaa gcatggctgg | 840 | |
| accaagttta tctctatgca gtctctttac aacctcatca accgggagga cgagcgggaa | 900 | |
| ctcaactggt actgcaacaa gactggtgtt ggtctcattc cctggtctcc tctggctcga | 960 | |
| ggcattcttg cgcgacccag aagtgctgag gacactgctc ggtccggttc tgatctgcga | 1020 | |
| atgatgctgt tcgacaagga ccacgactcc actgccgaga tcatcgaccg ggtcgagaag | 1080 | |
| atggccaaga agaagggcgt tgccatggcc acaatcgcca ccgcctgggt ccttcacaag | 1140 | |
| ggtgccatgc ccattgttgg tttctcgtcc gagaagcgaa tggatgaggc tctggccgcc | 1200 | |
| ctggacgttg agtttgatgc catggacttg aagtacctcg aggatgctta cgagcccgtc | 1260 | |
| aagtacaaga tgtaa | 1275 | |

<210> SEQ ID NO 9
<211> LENGTH: 1146
<212> TYPE: DNA
<213> ORGANISM: Yarrowia lipolytica
<220> FEATURE:
<221> NAME/KEY: gene
<222> LOCATION: (1)..(1146)
<223> OTHER INFORMATION: FADH gene

<400> SEQUENCE: 9

| | | |
|---|---|---|
| atgtctaccg aaggaaagac catcacttgc aaggccgccg ttgcctggga ggccggcaag | 60 | |
| cccctgaccc ttgaagacgt cgaggttgct cctccccagg cccacgaggt tcgagtcaag | 120 | |
| gtcacctaca ctggtgtctg ccacaccgac gcctacactc tcagtggctc tgatcccgag | 180 | |
| ggaatcttcc cctctgttct gggccacgag ggtgccggta cgtcgagtc tatcggcgag | 240 | |
| ggcgtcacca gcgtcaagcc cggagactcc gtcattctgc tctacactgc cgagtgcaag | 300 | |
| gagtgcaagt tctgcaagtc cggcaagacc aacctgtgcc agaaggtgcg agccacccag | 360 | |
| ggtaagggtg ttctgccaga cggaaccacc cggttcaagt gcaagggcaa ggatctctat | 420 | |
| tcgtatatgg gctgctcttc cttctcccag tacactgtgg ttgctgacgt ctccctcgtc | 480 | |
| gccgtcgacc cctctgctcc ccaggaccga acctgtctgc tcggctgcgg tgtcaccacc | 540 | |
| ggctacggag ctgccaccgt caccgccaat gtccagaagg gcgacaatgt tgctgtcttc | 600 | |
| ggcgctggct gtgtcggtct ggccgtcgtg atgggcgcca aggagcgagg agccgccaag | 660 | |
| atcattgtca ttgacatcaa tggcaacaag gaggcttggg cttacaagtt tggtgccact | 720 | |
| gactttgtca accccaccaa gctacccgag ggcaccacta ttgttgacaa gctggtggag | 780 | |
| atgaccgacg gaggttgcga cttcaccttt gactgtaccg aaacgtgac tgtcatgcga | 840 | |
| caggctctgg aggcctgcca taagggctgg ggtgagtcga tcatcatcgg cgttgctgct | 900 | |
| gctggccagg agattgccac ccgacctttc cagctcgtca ccggccgagt gtggaagggc | 960 | |
| tctgccttg gcggtgtcaa gggccgaacg cagctgcccg agattgtcaa gcgatacaag | 1020 | |
| gacggctctt tcgagattga caacttcatc acccactcca agcccctcaa ggacatcaac | 1080 | |
| tctgccttca ccgacctgca caagggcgac tgcattcgaa ccgtcgtcga catgtggcag | 1140 | |

```
                                      -continued
gtttag                                                                  1146

<210> SEQ ID NO 10
<211> LENGTH: 1830
<212> TYPE: DNA
<213> ORGANISM: Yarrowia lipolytica
<220> FEATURE:
<221> NAME/KEY: gene
<222> LOCATION: (1)..(1830)
<223> OTHER INFORMATION: FAO1 gene

<400> SEQUENCE: 10
atgtctgacg acaagcacac tttcgacttt atcattgtcg gtggaggaac cgccggcccc        60
actctcgccc ggcgactggc cgatgcctgg atctccggta agaagctcaa ggtgctcctg       120
ctcgagtccg gcccctcttc cgagggtgtt gatgatattc gatgccccgg taactgggtc       180
aacaccatcc actccgagta cgactggtcc tacgaggtcg acgagcctta cctgtctact       240
gatggcgagg agcgacgact ctgtggtatc ccccgaggcc attgtctggg tggatcctct       300
tgtctgaaca cctctttcgt catccgagga acccgaggtg atttcgaccg aatcgaagag       360
gagaccggcg ctaagggctg gggttgggat gatctgttcc cctacttccg aaagcacgag       420
tgttacgtgc cccagggatc tgcccacgag cccaagctca ttgacttcga cacctacgac       480
tacaagaagt ccacggtgga ctctggtcct atcaaggtcc agccttacga ctacgcgccc       540
atctccaaga agttctctga gtctctggct ctttcggct acccttataa ccccgagatc       600
ttcgtcaacg gaggagcccc caggggttgg ggtcacgttg ttcgttccac ctccaacggt       660
gttcgatcca ccggctacga cgctcttgtc cacgccccca gaacctcga cattgtgact        720 ggccacgctg tcaccaagat tctctttgag aagatcggtg gcaagcagac cgccgttggt       780
gtcgagacct acaaccgagc tgccgaggag gctgggccta cctacaaggc ccgatacgag       840
gtggttgtgt gctgcggctc ttatgcctct ccccagcttc tgatggtttc cggtgttgga       900
cccaagaagg agctcgagga ggttggtgtc aaggacatca ttttggactc tccttacgtt       960
ggaaagaacc tgcaggacca tcttatctgc ggtatctttg tcgaaattaa ggagcccgga      1020
tacacccgag accaccagtt cttcgacgac gagggactcg acaagtccac cgaggagtgg      1080
aagaccaagc gaaccggttt cttctccaat cctccccagg gcatttttctc ttacggccga    1140 atcgacaacc tgctcaagga tgatcccgtc tggaaggagg cctgcgagaa gcagaaggct      1200
ctcaaccctc gacgagaccc catgggtaac gatccctctc agccccattt cgagatctgg      1260
aatgctgagc tctacatcga gctagagatg acccaggctc ccgacgaggg ccagtccgtc      1320
atgaccgtca tcggtgagat tcttcctcct cgatccaagg gttacgtcaa gctgctgtcc      1380
cccgacccta tggagaaccc cgagattgtc cacaactacc tgcaggaccc tgttgacgct      1440
cgagtcttcg ctgccatcat gaagcacgcc gccgacgttg ccaccaacgg tgctggcacc      1500
aaggacctcg tcaaggctcg atggccccg gagtccaagc ccttcgagga aatgtccatc       1560
gaggaatggg agacttacgt ccgagacaag tctcacacct gtttccaccc ctgtggtact      1620
gtcaagcttg gtggtgctaa tgataaggag gccgttgttg acgagcgact ccgagtcaag      1680
ggtgtcgacg gcctgcgagt tgccgacgtc tctgtcctc cccgagtccc caacggacac       1740
acccaggctt ttgcctacgc tgttggtgag aaggctgccg acctcatcct tgccgacatt     1800
gctggaaagg atctccgacc tcgaatctaa                                      1830

<210> SEQ ID NO 11
<211> LENGTH: 1602
```

```
<212> TYPE: DNA
<213> ORGANISM: Yarrowia lipolytica
<220> FEATURE:
<221> NAME/KEY: gene
<222> LOCATION: (1)..(1602)
<223> OTHER INFORMATION: FALDH1 gene

<400> SEQUENCE: 11
atgtcctggg aaacaatcac tcctcctacg ccaatcgata cgtttgacag caacttgcaa      60
cgtcttcgag actctttcga gaccggcaag ctcgactctg tcgactaccg tctcgagcag     120
ctgcgaaccc tgtggttcaa gttctacgac aacctcgaca acatctacga ggcggtcacc     180
aaggatctcc atcgacccag gttcgaaacc gagctcaccg aggtactgtt tgttcgagac     240
gagttctcca ccgtcatcaa gaacctgcga aagtgggtca aggaagaaaa ggtggagaac     300
cccggaggcc ccttccagtt tgccaacccc cgaatccgac ccgttcctct gggagtggtg     360
ctggtcatca ctccctggaa ctaccccgtc atgctcaaca tctcacctgt gattgccgcc     420
attgctgccg gctgtcccat cgtgctcaag atgtccgagc tgtctcccca cacttccgct     480
gttcttggcc gaatcttcaa ggaggccctg accccggta tcatccaggt tgtttacgga     540
ggtgtccccg agaccaccgc ccttcttacc cagcattggg acaagatcat gtacaccgga     600
aacggagccg ttggtcgaat catcgcccag gccgcggtca agaacctgac tcctctagct     660
cttgagcttg gtggcaagtc acccgtgttc atcacttcca actgcaagag cgttatgacg     720
gccgctcggc gaatcgtgtg gggcaagttt gtcaacgccg ccagatctg tgtcgctcca     780
gactacattc tggttgctcc cgaaaaggag gccgagctcg tcgcttgtat caaggaggtg     840
ctccaagaac gatacggctc caagagagac gcccaccacc ccgatctgtc ccatatcatt     900
tccaagcccc attggaagcg tattcacaac atgatcgccc agaccaaggg agacatccag     960
gtgggtggac tcgagaacgc cgacgaagac caaaagttca tccagcccac aatcgtctcc    1020
aacgttccag atgacgacat tctcatgcag gacgagattt tcggacccat catccccatc    1080
atcaagcccc gaaccctcgg ccagcaggtt gattacgtca aagaaacca tgacaccccc    1140
ctggccatgt acatcttctc tgacgacccc aaggaggtgg actggctaca gacccgaatc    1200
cgagctggtt ctgtaaacat caacgaggtc attgagcagg tcggactggc ctctctgcct    1260
ctcagtggag ttggagcttc cggaaccgga gcataccatg gaaaattctc cttcgatgtc    1320
ttcacccaca gcaggccgt tatgggacag cccacctggc ccttctttga atacctcatg    1380
tattaccggt accctcctta ctccgagtac aagatgaagg tgctccgaac cctgttccca    1440
ccggttctga ttcctcgaac cggccgaccc gacgctactt tcttcagcg agttctcggc    1500
aacaagctgc tttggatcat tattgccgcc cttgttgcgt acgccaaacg aaatgagctg    1560
ctcatcacca ttgctcagat tatgtcggtg tttattaagt ag                       1602

<210> SEQ ID NO 12
<211> LENGTH: 1566
<212> TYPE: DNA
<213> ORGANISM: Yarrowia lipolytica
<220> FEATURE:
<221> NAME/KEY: gene
<222> LOCATION: (1)..(1566)
<223> OTHER INFORMATION: FALDH2 gene

<400> SEQUENCE: 12
atgtcagagt tcgattggga gtcaattttg ccggcaacac cactaggtga gatcgagaag      60
gatattcaaa ccctacgaca gggcttcagg tccggaaaga cgctggattt gaacttcagg     120
```

-continued

```
cttgaccaga ttcgtaagct tttctatgct ctctatgata atgtcgatgc gatcaaagaa    180
gcaattcata aggatctcgg acgtccggtc ttcgagactg aactttgcga gatctccttt    240
cagtggggtg aattcaataa tgtcgtttct aacttgaaga aatgggcagc tgatgagacg    300
gtgaagggaa ccaccattca atacactctc acccggccaa agattagaaa gcgtccactt    360
ggtaccgtcc ttatcatatc tccttggaac tacccatttg ttctgaccat ctctcccctg    420
cttgctgctc tagcggcagg aaatacggtg gccctaaagt tctccgaaat gtgcccacat    480
acatcgcttt tgctgggaaa gttgtgcaca gaggcacttg ataaagaaat tttcaaggca    540
tttcagggag gcgttccggt agtgtcgag attctcaagt acaagttcga caaaatcatg    600
tacactggaa atcatcgagt tggcaagatc atcttggacg cagctaacaa atacctcacc    660
cccgttattt tggagcttgg aggcaaatca ccagtcttcg tgactaagaa ttgccaaaac    720
gtatctcttg ctgccaagcg tgctctgtgg ggtaaactgg tcaacgctgg acaaacatgc    780
gttgccccg attacatcat cgtcgagcct gaggtcgaac aggagtttat caaagcttgc    840
cagtactggg ttgagaagtt ctaccgaggt ggagttgact ctgatcataa ggacttcact    900
catattgcaa cacctggaca ttggagacga ttgacatcca tgcttgccca gacagaggga    960
aatatcatca caggcggaaa ttcggacgag aaatcacggt tcttgctcc cacagttgtt   1020
gcgaaagttc ctgatggtga ttctttgatg aatgatgaga tctttggccc tatcctgccc   1080
atcctgacag ccagatccgt tgacgaaggt attcgctatg ttcatgagaa tcacgacact   1140
cccctggcca tgtatgtctt tactgataat gcatcagaag gagagtatat ccaatctcaa   1200
atcaactcag gtggcctgat attcaatgat agtcttgttc acgttggctg cgtgcaggcg   1260
ccttttggtg gtgtcggcca atccggctat gggtcttatc acggcgaaga ttccttcttg   1320
gcttttcac acaggcagac tttcatgaag cagcccatt tcatcgaacg accaatggcg   1380
atcagatatg cccctacac tagtcgaaaa caaaaggctg tccagggtag tctagctgct   1440
ccatcttttc ctcgaacagg aaaggttgac cgctccctgt tggagcggat atttggtaag   1500
ctatggttct gggtgatcgt tttagggcta ggagcagcca gtttgaagtc aggaattttc   1560
ttatga                                                             1566
```

<210> SEQ ID NO 13
<211> LENGTH: 1590
<212> TYPE: DNA
<213> ORGANISM: Yarrowia lipolytica
<220> FEATURE:
<221> NAME/KEY: gene
<222> LOCATION: (1)..(1590)
<223> OTHER INFORMATION: FALDH3 gene

<400> SEQUENCE: 13

```
atgactacca ctgccacaga acccccacg acaaacgtga cccccaccac gtcactgccc     60
aaggagaccg cctccccagg agggaccgct tctgtcaaca cgtcattcga ctgggagagc   120
atctgcggca agacgccgtt ggaggagatc gagtcggaca tttcgcgtct caaaaagacc   180
ttccgatcgg gcaaaactct ggatctggac taccgactcg accagatccg aaacctggcg   240
tatgcgatcc gcgataacga aaacaagatc cgcgacgcca tcaaggcgga cctgaaacga   300
cctgacttcg aaaccatggc ggccgagttc tcggtccaga tgggcgaatt caactacgtg   360
gtcaaaaacc tgccgaaatg ggtcaaggac gaaaaagtca agggaaccag catggcgtac   420
tggaactcgt cgccaaagat ccggaaacgg cccctgggct ccgtgcttgt catcacgccc   480
tggaactacc cactgattct ggccgtgtcg cctgttctgg gcgccattgc cgcaggcaac   540
```

```
accgtggcgc tgaaaatgtc agaaatgtca cccaacgcgt caaaggtgat tggcgacatt    600
atgacagctg ccctggaccc ccagctcttt caatgcttct tcggaggagt ccccgaaacc    660
accgagatcc tcaaacacag atgggacaag atcatgtaca ccggaaacgg caaagtgggc    720
cgaatcatct gtgaggctgc caacaagtac ttgacacctg tggagctcga actcggagga    780
aagtcgcctg ttttcgtcac caaacactgc tccaacctgg aaatggccgc ccgccgaatc    840
atctggggca aattcgtcaa cggaggacaa acctgcgtgg ctccagacta cgttctggtg    900
tgtcccgagg tccacgacaa atttgtggct gcctgtcaaa aggtgctgga caagttctac    960
cctaacaact ctgccgagtc cgagatggcc catatcgcca cccctctcca ttacgagcgt   1020
ttgacgggcc tgctcaattc cacccgaggt aaggtcgttg ctggaggcac tttcaactcg   1080
gccacccggt tcattgctcc tacgattgtc gacggagtgg atgccaacga ttctctgatg   1140
cagggagaac tgtttggtcc tcttctcccc attgtcaagg ccatgagcac cgaggctgcc   1200
tgcaactttg tgcttgagca ccaccccacc ccctggcag agtacatctt ttcagataac   1260
aattctgaga ttgattacat ccgagatcga gtgtcgtctg gaggtctcgt gatcaacgac   1320
actctgatcc acgtgggatg cgtacaggcg ccctttggag tgtcggaga cagtggaaat   1380
ggaggatacc atggcaagca cactttcgat tgttcagcc attctcagac ggtcctcaga   1440
caacccggat gggtcgaaat gctgcagaag aaacggtatc ctccgtacaa caagagcaac   1500
gagaagtttg tccggagaat ggtggtcccc agccctggtt ttccccggga gggtgacgtg   1560
agaggatttt ggtcgagact cttcaactag                                    1590
```

<210> SEQ ID NO 14
<211> LENGTH: 1560
<212> TYPE: DNA
<213> ORGANISM: Yarrowia lipolytica
<220> FEATURE:
<221> NAME/KEY: gene
<222> LOCATION: (1)..(1560)
<223> OTHER INFORMATION: FALDH4 gene

<400> SEQUENCE: 14

```
atgtctacct tgattgggga atccattgtg cctgccactc ctctcgacca gattcctggc     60
gacatccagc gactgcgaaa gggcttccga tccggaaaga ccctcgatct caactaccga    120
ctggaccaga ttcgaaactt gcactacgtc ctcagagaca atgtcgaggc catcaaggac    180
gccgtgtaca aggatctcgg ccgacccaag cacgagactg acctgtgcga ggtgggtttc    240
ctgtggggcg agtttaacaa cgtggttgcc aacctcaaga agtgggccgc cgacgaggac    300
gtcaagacca acctgcagta ctccatctcc tcccccaaga tccgaaagcg acctcttgga    360
aacgtgctca tcatctcgcc ctggaactac cctttatgc tgaccgtgtc tcctctcatt    420
ggagctctgg ctgccggtaa cactgtggct gtcaagttct ccgaaatggc cccccacact    480
tccaaaattg ttggcgactt gtgcaccaag gccctcgacc ccgacgtctt ccaggccatc    540
cagggaggtg tccccgtcgt caccaagacc ctcgagcaga agttcgacaa gattatgtac    600
actggtaacc acactgtcgg taagatcatt gccactgccg ccaacaagta cctgacaccc    660
gtcatcctcg agctcggagg taagtcgccc gttttttgtca ccaagaactg caagaacatc    720
aagcttgccg ctaagcgagc cctgtgggt aaggtggtaa acgctggcca gacctgtgtg    780
gctcccgact acgtgattgt cgagcccgag gtggagcagg agtttatcga cgcctgcaag    840
tactggatta acgagttcta cagtggtaag attgaccagt acaaccccga ctttgccaag    900
```

| | |
|---|---|
| atcgccaccc ccaaccactg gaaccgactt acctccatgt tgagcaagtc caagggagag | 960 |
| atcattactg gaggtaacac tgacgagaag actcgattca tcgctcctac tgtcgtcgca | 1020 |
| aaggtccccg acaatgattc cctgatggag gacgagattt tcggccctct tctgcccatt | 1080 |
| ctcactgccc gatccgtcga ggagggtatc aagtacgtgc acgagaacca cgacacccct | 1140 |
| cttgccatgt acgtcttcac tgacaaggcc tctgagggcg actacatcca gtcccagatc | 1200 |
| aactctggtg gccttatctt caatgacact ctgatccacg ttggatgtgt ccaggctccg | 1260 |
| tttggtggtg tcggcatgtc cggttacggt gcttaccatg gcgaggactc cttcctggcc | 1320 |
| ttcacccacc gacaaaccta cctcaaccag cccaagcttc tggagcctct tcaggacgtg | 1380 |
| cgatacgccc cctacaccaa aaccaagcga agcatggtca agaacctgct gctggtcggc | 1440 |
| cccattttcc cccgaaccgg ctccgtatac cccaacgtgc tgatccgaat cttccgaaag | 1500 |
| atttggttct gggtccttat tgtcgccatc ggagctgctg gtgccaaggc tctgctctag | 1560 |

<210> SEQ ID NO 15
<211> LENGTH: 2034
<212> TYPE: DNA
<213> ORGANISM: Yarrowia lipolytica
<220> FEATURE:
<221> NAME/KEY: gene
<222> LOCATION: (1)..(2034)
<223> OTHER INFORMATION: ACO1 gene

<400> SEQUENCE: 15

| | |
|---|---|
| atggccaagg agcgaggtaa gactcaattc actgtccgag atgtgaccaa cttcctcaat | 60 |
| ggtggagaag aagagaccca gattgtcgag aagatcatga gcagtattga acgtgatcca | 120 |
| gtactgtctg tcactgctga ctacgactgc aaccttcagc aggcccgaaa acagaccatg | 180 |
| gagcgggtgg ctgctctgtc gccttatctg gtcaccgata ctgagaagct atctctgtgg | 240 |
| cgtgcgcaac tgcatggaat ggttgatatg tctactcgta cgcggttgtc gatccacaac | 300 |
| aacctgttca ttggttccat caggggatct ggtactcctg aacagttcaa gtactgggtc | 360 |
| aagaagggag cggtggctgt taagcagttc tatggatgct ttgccatgac agagttgggc | 420 |
| catggaagca acctcaaggg actagagaca accgccactt atgaccagga cagtgaccag | 480 |
| ttcattatca cactcctca tattggtgct accaagtggt ggattggcgg tgcagcccac | 540 |
| acttccaccc attgtgtttg tttcgcgaaa ctgattgtgc atggcaagga ctatggtact | 600 |
| cgaaactttg tggtacctct ccgaaatgtc cacgatcaca gtctcaaggt cggtgtttca | 660 |
| attggagaca ttggaaagaa gatgggcaga gatggtgttg acaatggctg gatccagttc | 720 |
| accaatgttc gaatccccag acagaacatg ctaatgagat atgccaaggt gtctgatact | 780 |
| ggagtggtaa ccaaacccgc tcttgaccaa ctcacttatg gagccctcat tcgaggtcga | 840 |
| gtgtccatga ttgccgactc gttccacgtc tccaaacgat tcctcacaat tgctcttcgg | 900 |
| tacgcttgtg tccgacgaca gtttggaacc tctggagaca ctaaggagac caagatcatc | 960 |
| gactacccctt accaccagcg acgattgctg cctcttctgg cctactgcta cgctatgaag | 1020 |
| atgggtgctg atgaggctca gaagacttgg attgagacca ccgatcgaat tctggctctc | 1080 |
| aatcccaacg accccgccca agaacgat ctggagaagg ccgtcaccga cacaaaggag | 1140 |
| ctgtttgctg cgtctgcagg aatgaaggca tttaccacgt ggggatgtgc caaaatcatt | 1200 |
| gatgagtgcc gacaggcctg tggaggtcat ggatactctg gatataacgg atttggccag | 1260 |
| ggctacgctg actgggttgt ccagtgtacc tgggaaggac acaacaacgt tctgtgtctg | 1320 |
| tcaatgggcc gagggctggt tcagtcagct ctacagattt tggctggaaa gcacgtcggt | 1380 |

```
gcttctattc agtacgtagg agacaagtct aaaatctccc agaacggcca gggtaccccc    1440
agagagcaac ttctgtcccc cgagtttcta gtagaagctt tcagaacggc ttctcgaaac    1500
aacattctca gaaccaccga taaataccaa gagcttgtca aaactctcaa tcccgaccag    1560
gcctttgagg agctgtctca gcagagattc cagtgtgctc gaatccacac acgacagcat    1620
cttatctctt cattctatgc ccgaattgcc actgccaaag acgatatcaa gccccatctg    1680
ctgaaactgg ccaatctgtt tgccctctgg tcaattgagg aggacactgg aatcttcctg    1740
cgggagaaca tcctcacccc tggagacatt gacctgatca acagtcttgt ggacgagctc    1800
tgtgttgcag ttcgagatca ggtaattgga ctcactgatg cctttggtct ctctgacttc    1860
ttcattaacg ctcccatcgg ctcctacgat ggtaatgttt acgaaaagta ctttgccaag    1920
gtcaaccagc aaaaccccgc tactaaccct cgtcctccct actacgagtc gactctcaag    1980
cccttcttgt tccgagaaga ggaggacgat gaaatttgcg atctcgatga gtga          2034
```

<210> SEQ ID NO 16
<211> LENGTH: 2103
<212> TYPE: DNA
<213> ORGANISM: Yarrowia lipolytica
<220> FEATURE:
<221> NAME/KEY: gene
<222> LOCATION: (1)..(2103)
<223> OTHER INFORMATION: ACO2 gene

<400> SEQUENCE: 16

```
atgaacccca acaacactgg caccattgaa atcaacggta aggagtacaa caccttcacc     60
gagccccccg tggccatggc tcaggagcga gccaagacct ccttcccccgt gcgagagatg   120 acctacttcc tcgacggtgg cgagaagaac accctcaaaa acgagcagat catggaggag   180
attgagcgag accctctttt caacaacgac aactactacg atctcaacaa ggagcagatc   240
cgagagctca ccatggagcg agtcgccaag ctgtctctgt ttgtgcgtga tcagcccgag   300
gacgacatca agaagcgatt tgctctcatt ggtatcgccg atatgggaac ctacacccga   360
cttggtgtcc actacggcct cttctttggc gccgtccgag gtaccggaac tgccgagcag   420
tttggccact ggatctccaa gggagccgga gacctgcgaa agttctacgg atgtttctcc   480
atgaccgagc tgggccatgg ctccaacctg gctggtctcg agaccaccgc catctacgat   540
gaggagaccg acgagttcat catcaacacc cctcacattg ccgccaccaa gtggtggatt   600
ggaggagccg cccacaccgc cacccacact gtcgtgttcg cccgactcat tgtcaagggc   660
aaggactacg gtgtcaagac ctttgttgtc cagctgcgaa acatcaacga ccacagcctc   720
aaggtcggta tctctattgg tgatatcgga aagaagatgg ccgagacggt atcgataac    780 ggatggatcc agttccaccaa cgtgcgaatc ccccgacaga acctgctcat gaagtacaca   840
aaggtcgacc gagagggtaa cgtgacccag cctcctctgg ctcagcttac ctacggttct   900
cttatcactg gtcgagtctc catggcctct gattctcacc aggtcggaaa gcgattcatc   960
accattgctc tgcgatacgc ctgcattcga cgacagttct ccaccacccc cggccagccc   1020
gagaccaaga tcatcgacta ccctactcat cagcgacgac ttctgcctct tctggcctat   1080
gtctatgctc ttaagatgac tgccgatgag gttggagctc tcttctcccg aaccatgctt   1140
aagatggacg acctcaagcc cgacgacaag gccggcctca atgaggttgt tccgacgtc    1200 aaggagctct tctccgtctc cgccggtctc aaggccttct ccacctgggc ttgtgccgac   1260
gtcattgaca agacccgaca ggcttgcggt ggccacggtt actctggata caacggtttc  1320
```

| | |
|---|---|
| ggccaggcct acgccgactg ggttgtccag tgcacctggg agggtgacaa caacattctc | 1380 |
| acccttctg ccggccgagc tcttatccag tctgccgttg ctctgcgaaa gggcgagcct | 1440 |
| gttggtaacg ccgtttctta cctgaagcga tacaaggatc tggccaacgc taagctcaat | 1500 |
| ggccgatctc tcaccgaccc caaggtcctc gtcgaggcct gggaggttgc tgccggtaac | 1560 |
| atcatcaacc gagccaccga ccagtacgag aagctcattg gcgagggtct taacgccgac | 1620 |
| caggcctttg aggttctgtc tcagcagcga ttccaggccg ccaaggtcca cacgacga | 1680 |
| cacctcattg ccgctttctt ctcccgaatt gacaccgagg ctggcgaggc catcaagcag | 1740 |
| cccctgctta acctggctct gctgtttgcc ctgtggtcca tcgaagagga ctctggtctg | 1800 |
| ttcctgcgag agggcttcct cgagcccaag gatatcgaca ccgtcaccga gctcgtcaac | 1860 |
| aagtactgca ccactgtgcg agaggaggtc attggctaca ccgatgcctt caacctgtcc | 1920 |
| gactacttca tcaacgctcc tattggatgc tacgatggtg acgcttaccg acactacttc | 1980 |
| cagaaggtca cgagcagaa ccctgcccga gaccccgac ctccttacta cgcctctact | 2040 |
| ctcaagccct ccttttccg agaggaggag gatgatgaca tttgcgagct tgatgaggaa | 2100 |
| tag | 2103 |

<210> SEQ ID NO 17
<211> LENGTH: 2103
<212> TYPE: DNA
<213> ORGANISM: Yarrowia lipolytica
<220> FEATURE:
<221> NAME/KEY: gene
<222> LOCATION: (1)..(2103)
<223> OTHER INFORMATION: ACO3 gene

<400> SEQUENCE: 17

| | |
|---|---|
| atgatctccc ccaacctcac agctaacgtc gagattgacg gcaagcagta caacaccttc | 60 |
| acagagccac ccaaggcgct cgccggcgag cgagccaagg tcaagttccc catcaaggac | 120 |
| atgacggagt ttctgcacgg tggcgaggag aacgtgacca tgatcgagcg actgatgacg | 180 |
| gagctcgagc gagaccccgt gctcaacgtg tcgggcgact acgacatgcc caaggagcag | 240 |
| ctgcgagaga cggccgtggc gcgaattgcg gcgctgtccg gccactggaa gaaggacaca | 300 |
| gaaaaggagg cgctgctgcg gtcccagctg cacggcattg tggacatggg cacccgaatc | 360 |
| cgactcggtg tgcacacggg cctgttcatg ggcgccatcc ggggttccgg caccaaggag | 420 |
| cagtacgact actgggtgcg aaagggcgcc gcggacgtca agggcttcta cggctgcttt | 480 |
| gctatgaccg agctgggcca tgctccaac gtggccggtc ttgagaccac cgccacctac | 540 |
| atccaggaca cggacgagtt catcatcaac accccccaaca ctggagccac caagtggtgg | 600 |
| attggaggag ccgcccactc ggccaccac accgcctgct tgctcgtct gcttgtcgac | 660 |
| ggcaaggact acggcgtcaa gatctttgtt gtccagctgc gagacgtctc ttctcactct | 720 |
| ctcatgcccg gcatcgctct cggcgacatt ggaaagaaga tgggccgaga cgccatcgac | 780 |
| aacggctgga tccagttcac caatgtgcga atcccccgac agaacatgct catgaagtac | 840 |
| gccaaggtct cgtctaccgg caaggtgtcg cagcctcctc tggcccagct cacctacggc | 900 |
| gctctcattg gcggccgagt caccatgatt gccgactcct ctttgtctc ccagcgattc | 960 |
| atcaccattg ctctgcgata cgcctgtgtg cgacgacagt ttggcaccac cccgggccag | 1020 |
| cccgagacta agatcatcga ctaccctac catcagcgac gtctgctgcc tcttctggcc | 1080 |
| ttcacctacg ccatgaagat ggccgccgac cagtccagaa ttcagtacga tcagaccacc | 1140 |
| gatctgctgc agaccatcga ccctaaggac aagggcgctc tgggcaaggc cattgtcgac | 1200 |

```
ctcaaggagc tgtttgcctc ttctgctggt ctcaaggcct tcaccacctg gacctgtgcc   1260
aacatcattg accagtgccg acaggcctgc ggtggccacg gctactctgg ctacaacggc   1320
tttggccagg cctacgccga ctgggttgtc cagtgcacct gggagggtga caacaacgtc   1380
ctgtgtctgt ccatgggccg aggtctcatc cagtcgtgtc tgggccaccg aaagggtaag   1440
cctctgggct cttctgtcgg ctacctggct aacaagggtc ttgagcaggc tactctgagc   1500
ggccgagacc tcaaggaccc caaggttctc atcgaggcct gggagaaggt cgccaacggc   1560
gccatccagc gggccactga caaatttgtc gagctcacca agggcggcct ctctcctgac   1620
caggcctttg aggagctgtc gcagcagcga ttccagtgtg ccaagatcca cacccgaaag   1680
cacctggtga ctgccttcta cgagcgaatc aacgcctctg cgaaggccga cgtcaagcct   1740
tacctcatca acctcgccaa cctcttcact ctgtggtcca ttgaggagga ctctggtctc   1800
ttcctgcgag agggtttcct gcagcccaag gacattgacc aggtgactga gctggtgaac   1860
cactactgca aggaggttcg agaccaggtt gccggctaca ccgatgcctt tggtctgtct   1920
gactggttca tcaacgctcc cattggaaac tacgatggtg acgtttacaa gcattacttt   1980
gccaaggtta accagcagaa ccctgctcag aaccccgac  ctccttacta tgagagcact   2040
cttcgacctt tcctgttccg agaggatgag gatgacgaca tttgcgagct ggacgaggaa   2100
tag                                                                 2103

<210> SEQ ID NO 18
<211> LENGTH: 2106
<212> TYPE: DNA
<213> ORGANISM: Yarrowia lipolytica
<220> FEATURE:
<221> NAME/KEY: gene
<222> LOCATION: (1)..(2106)
<223> OTHER INFORMATION: ACO4 gene

<400> SEQUENCE: 18
atgatcaccc caaaccccgc taacgacatt gtccatgacg gcaagctcta cgacaccttc     60
actgagcccc ccaagctgat ggctcaggag cgagctcagc tggacttcga ccctagagac    120
atcacctact ttctggatgg ctctaaggag gagaccgagc tgctggagtc gctcatgctc    180
atgtacgagc gagaccctct cttcaacaac cagaacgagt acgatgaatc gtttgaaaca    240
ctgcgagagc gatctgtgaa gcgaattttc cagctgtcca gtccatcgc  catggacccc   300 gagcccatgt ctttccgaaa gattgggttc ctgggtattc ttgacatggg aacgtatgct    360
cgactgggag tccactacgc gctcttctgt aactccatcc ggggccaggg aacccccgat    420
cagctcatgt actggctgga ccagggagcc atggtcatca agggcttcta cggctgtttt    480
gccatgaccg aaatgggcca tggatctaac ctgtcgcgtc tggaaaccat cgccactttc    540
gacaaagaga ccgacgaatt tatcattaac acgccccacg ttggagccac aaagtggtgg    600
attggtggtg ctgctcacac tgctactcac acacttgcct tgcccgtct  tcaagtagac    660 ggaaaggact acggtgtgaa atcgtttgtc gtacctctcc gaaacctgga cgaccattcg    720
ctgcgtcctg gaatcgccac aggtgatatt ggtaagaaga gggtcgaga  tgccgttgac    780 aacggctgga ttcagttcac caacgtccga gtgccccgaa actacatgct catgaagcat    840
accaaggttc ttcgagacgg taccgtcaag cagccgcctt ggcccaact  gacttacgga    900 tctctcatca ctggacgagt ccagatgacc actgactctc acaatgtgtc caaaaagttc    960
ctcaccattg ccctgagata cgccaccatc cgacgacagt tctcgtcaac tccaggagag   1020
```

```
cccgaaaccc gactaattga ctacctgtac caccaaagac gactcctgcc tcttatggct    1080
tactcttacg ccatgaaact agctggagat cacgtccgag agctgttctt tgcatcccag    1140
gagaaggctg agagcctcaa ggaggacgac aaagccggag ttgagtctta cgtccaggat    1200
atcaaggagc tcttctctgt ttctgctggt ctcaaggctg ccactacatg gcttgtgct     1260 gacatcattg acaaggcccg acaggcgtgt ggaggccacg atactctgc ctacaacggc     1320 tttggacagg ccttccagga ctgggttgtc cagtgcactt gggagggtga caatactgtt    1380
ctgactctat ctgccggccg agctctgatc caatctgctc tcgtctaccg aaaggagggc    1440
aaactaggta acgccacgaa gtacctctct cggtccaagg agcttgccaa cgccaagaga    1500
aacggacgat ccctggaaga ccccaagctg ctcgtggagg catgggaggc tgtctctgcc    1560
ggtgctatca acgctgctac tgacgcttac gaggagctct ccaagcaggg agtttctgtt    1620
gacgagtgct ttgagcaggt gtcccaggag cgattccagg ctgcccgaat ccacactcga    1680
cgagctctta tcgaggcctt ctactcacga atcgccactg ctgatgagaa ggtgaagcct    1740
catctgatcc ctctggccaa cctgtttgcc ctgtggtcca ttgaggagga ctctgctctg    1800
ttcctggctg agggctactt tgagcctgag atatcattg aggtgacttc tcttgtcaac     1860
aagtactgcg gaattgttcg aaagaacgtt attggataca ccgatgcctt caacctgtcc    1920
gactacttca tcaacgctgc cattggacga tacgacggag acgtgtacaa gaactacttt    1980
gagaaggtca acagcagta ccctcctgag ggtggcaagc tcactacta cgaggatgtc      2040 atgaagccct tcctgcatcg agagcgaatt cccgatgtcc ccatggagcc cgaggatatt    2100
cagtaa                                                               2106
```

<210> SEQ ID NO 19
<211> LENGTH: 2100
<212> TYPE: DNA
<213> ORGANISM: Yarrowia lipolytica
<220> FEATURE:
<221> NAME/KEY: gene
<222> LOCATION: (1)..(2100)
<223> OTHER INFORMATION: ACO5 gene

<400> SEQUENCE: 19

```
atgaacaaca accccaccaa cgtgatcctt ggaggcaagg agtacgacac cttcaccgag    60
cctccggccc agatggagct ggagcgagcc aagacacaat tcaaggtccg agacgtgacc    120
aacttcctca caggcagcga gcaggagaca ctgctgaccg agcgaatcat gcgggagatt    180
gagcgagatc ccgttctcaa cgtcgccggc gactacgacg ccgatcttcc caccaagcga    240
cgacaagctg ttgagcgaat cggggctctg gcccgatacc tgcccaagga ttccgagaag    300
gaggccattt tgcgaggcca gctgcatggt attgtggaca tgggtacccg aacccgaatc    360
gccgttcact acggtctgtt tatgggcgcc attcgtggct caggaaccaa ggagcagtac    420
gattactggg tcgccaaggg cgccgctact ctgcacaaat ctatggctg ctttgccatg    480 actgagctgg gtcacggatc taacgtggcc ggtctcgaga ccaccgccac ccttgataag    540
gacaccgacg agttcatcat caacaccccc aactcgggag ccacaaagtg gtggattgga    600
ggagctgccc actctgctac ccacacggct tgtcttgccc gactcattgt tgatggcaag    660
gactatggtg ttaagatctt cattgttcag ctgcgagacc tcaactccca ctctctactc    720
aacggtattg ccattggaga tatcggcaag aagatgggcc gagatgccat tgataatggt    780
tggatccagt tcagacacgt ccgaattccc gacagaacaa tgctcatgcg atacgaccgg    840
gtgtctcgag acggcgaggt taccaccctc gagcttgccc agctcaccta cggagcactt    900
```

```
ctgtctggcc gagtgaccat gattgccgag tctcacctcc tgtctgctcg gttcctcacc      960
attgctcttc ggtacgcctg tatccgtcga cagttcggag ctgtgcctga caagcccgag     1020
actaagctca tcgactaccc ctaccaccaa cgacgtctgc tgcctcttct ggcctacacc     1080
tacgccatga agatgggcgc cgacgaggcc cagcagcagt acaactcctc ctttggcgct     1140
cttctcaagc tcaaccccgt caaggacgct gagaagtttg ctgtcgccac tgccgacctc     1200
aaggctctgt tgcctcttc tgccggaatg aaggccttca ccacctgggc tgccgccaag     1260
atcattgacg agtgccgaca ggcctgtggt ggccatggct actccggcta caacggtttc     1320
ggtcaggctt acgccgactg ggtcgtccaa tgcacttggg agggtgacaa caacgtgctg     1380
tgtctgtcca tgggtcgatc gctcatccag tcgtgcattg ccatgagaaa gaagaagggc     1440
catgtcggca gtcggtcga gtacctgcag cgacgagacg agctgcagaa tgcccgagtt     1500
gacaacaagc tctcactga ccctgctgtg ctcatcactg catgggagaa ggttgcctgc     1560
gaggccatca cagagccac tgactccttc atcaagctca cccaggaggg tctgtctcct     1620
gaccaggcct ttgaggagct gtctcaacag agatttgagt gtgcgcgaat ccacacccga     1680
aagcatctga tcacctcgtt ctacgctcga atctccaagg ccaaggcccg agtcaagccc     1740
caccttactg ttcttgccaa cctctttgcc gtctggtcca tcgaggagga ctctggtctc     1800
ttccttcggg agggctgctt cgagcctgcc gagatggacg agatcaccgc tctggtcgac     1860
gagctgtgct gcgaggctcg agagcaggtc attggattca ccgacgcctt caacctgtcc     1920
gacttcttca ttaacgcccc cattggccga ttcgacggag acgcctacaa gcactacatg     1980
gacgaggtca aggctgccaa caaccctcgt aacacccatg ctccttacta cgagaccaag     2040
ctgcgaccct tcctgttccg acccgatgag gacgaggaga tttgcgacct ggacgagtag     2100
```

<210> SEQ ID NO 20
<211> LENGTH: 2070
<212> TYPE: DNA
<213> ORGANISM: Yarrowia lipolytica
<220> FEATURE:
<221> NAME/KEY: gene
<222> LOCATION: (1)..(2070)
<223> OTHER INFORMATION: ACO6 gene

<400> SEQUENCE: 20

```
atgctctctc aacagtccct caacacgttt accgagcccc cggtcgaaat ggcccgggag      60
cgaaaccaga cttccttcaa cccgcgtctg ctgacgtact ttctggacgg aggcgaaaag     120
aacactctgc ttatggaccg actgatgcaa gagtacgagc gagaccctgt gtttcgaaac     180
gagggcgact acgatattac cgatgtggcc cagtcgcgag agctggcctt caagcgaatc     240
gccaagctca tcgagtatgt gcacaccgac gacgaggaga cgtatctgta ccgatgcatg     300
cttctgggcc aaatcgatat gggagccttt gcccggtacg ccatccacca cggagtctgg     360
ggcggtgcca ttcgaggtgc aggaacgcct gagcagtacg aattctgggt caagaaagga     420
tctctgtcgg ttaagaagtt ctatggatcc ttctccatga ccgagctggg ccacggcagt     480
aacttggtgg tctctggagac caccgccacc ctggacaaga acgcagacga gttcgtgatc     540
aacactccca acgttgctgc cactaaatgg tggatcggag gagccgccga taccgccact     600
cacacagctg tgtttgcacg tctcattgtc gacggagagg accacggtgt caagacgttt     660
gtggtgcagc tgcgagacgt ggagactcac aacctgatgc ctggtattgc tatcggagac     720
tgcggcaaga agatgggacg tcagggaacc gacaacggct ggatccagtt cacccatgtg     780
```

```
cgaattcccc gacagaacat gctcatgcga tactgtcacg tggacagcga cggaaatgtt      840
accgagccca tgatggctca gatggcctac ggagctcttc tggctggccg agtcggaatg      900
gccatggaca gttatttcac ctcgcgaaag ttccttacca ttgctcttcg atatgccacc      960
attcgacgag cttttgctgc cggaggaggt caggagacca agctgatcga ctacccttac     1020
caccagcgac gtctgctccc cctcatggcc cagacatatg ccatcaagtg caccgccgat     1080
aaggtcagag atcagttcgt caaggtcacc gacatgctcc taaacctcga tgtttctgac     1140
caagaggccg tgcccaaggc cattgccgag gctaaggagc tcttctctgt ttctgctggt     1200
gtcaaggcta ccacaacttg gcttgcgca cacaccattg accagtgcag acaggcgtgt     1260
ggaggccacg gatactctgc ttacaacggt tttggacgtg cttactccga ttgggtgatc     1320
cagtgcacct gggagggaga caataacatt ctgtgtctgt cagctggcag agctctggtc     1380
cagtctaacc gagctgtccg ggctggcaag cccattggag gtcctaccgc ctacctggct     1440
gctcccgctg gttcccccaa gctcgctggt cgaaacttgt acgacccaa ggtcatgatt     1500 ggggcctggg agactgtttc ccgagctctg atcaaccgaa ccaccgatga gtttgaggtg     1560
ctggccaaga agggtctgtc tactgcccag gcctacgagg agctgtccca gcaacgattc     1620
ctgtgtactc gaatccacac ccgtctgtac atggtcaaga acttctacga gcgaattgcc     1680
gaggagggca ccgagttcac caaggagcct cttaccagac ttgccaacct gtacgccttc     1740
tggtccgtcg aagaggaggc tggaatcttc ctccgagagg gctacatcac tccccaggag     1800
ctcaagtaca tcagtgccga gatccgaaag cagctcttgg aggtgcgaaa ggacgtcatt     1860
ggctacaccg atgccttcaa cgtgcctgat ttttcctca actctgccat ggacgagct     1920 gacggagatg tctacaagaa ctacttcaag gtggtcaaca ctcagaaccc tccccaagac     1980
cctcgacctc cttattacga gtctgtcatt agacccttcc tgttccgaaa ggacgaggat     2040
gaggaaattt gctctcttga ggatgagtag                                      2070
```

<210> SEQ ID NO 21
<211> LENGTH: 1205
<212> TYPE: DNA
<213> ORGANISM: Yarrowia lipolytica
<220> FEATURE:
<221> NAME/KEY: gene
<222> LOCATION: (1)..(1205)
<223> OTHER INFORMATION: Ura3 gene

<400> SEQUENCE: 21

```
cgcccagaga gccattgacg ttctttctaa tttggaccga tagccgtata gtccagtcta       60
tctataagtt caactaactc gtaactatta ccataacata tacttcactg ccccagataa      120
ggttccgata aaaagttctg cagactaaat ttatttcagt ctcctcttca ccaccaaaat      180
gccctcctac gaagctcgag ctaacgtcca caagtccgcc tttgccgctc gagtgctcaa      240
gctcgtggca gccaagaaaa ccaacctgtg tgcttctctg atgttaccca ccaccaagga      300
gctcattgag cttgccgata aggtcggacc ttatgtgtgc atgatcaaaa cccatatcga      360
catcattgac gacttcacct acgccggcac tgtgctcccc ctcaaggaac ttgctcttaa      420
gcacggtttc ttcctgttcg aggacagaaa gttcgcagat attggcaaca ctgtcaagca      480
ccagtaccgg tgtcaccgaa tcgccgagtg gtccgatatc accaacgccc acggtgtacc      540
cggaaccgga atcattgctg gcctgcgagc tggtgccgag gaaactgtct ctgaacagaa      600
gaaggaggac gtctctgact acgagaactc ccagtacaag gagttcctag tcccctctcc      660
caacgagaag ctggccagag gtctgctcat gctggccgag ctgtcttgca agggctctct      720
```

-continued

```
ggccactggc gagtactcca agcagaccat tgagcttgcc cgatccgacc ccgagtttgt    780
ggttggcttc attgcccaga accgacctaa gggcgactct gaggactggc ttattctgac    840
ccccggggtg ggtcttgacg acaagggaga cgctctcgga cagcagtacc gaactgttga    900
ggatgtcatg tctaccggaa cggatatcat aattgtcggc cgaggtctgt acggccagaa    960
ccgagatcct attgaggagg ccaagcgata ccagaaggct ggctgggagg cttaccagaa   1020
gattaactgt tagaggttag actatggata tgtaatttaa ctgtgtatat agagagcgtg   1080
caagtatgga gcgcttgttc agcttgtatg atggtcagac gacctgtctg atcgagtatg   1140
tatgatactg cacaacctgt gtatccgcat gatctgtcca atgggcatg ttgttgtgtt    1200 tctcg                                                              1205
```

<210> SEQ ID NO 22
<211> LENGTH: 36
<212> TYPE: DNA
<213> ORGANISM: Artificial Sequence
<220> FEATURE:
<223> OTHER INFORMATION: BglII F primer for HisG1

<400> SEQUENCE: 22
aattgggccc agatctcaga ccggttcaga caggat                36

<210> SEQ ID NO 23
<211> LENGTH: 36
<212> TYPE: DNA
<213> ORGANISM: Artificial Sequence
<220> FEATURE:
<223> OTHER INFORMATION: EcoRI R primer for HisG1

<400> SEQUENCE: 23
tctctgggcg gaattcggag gtgcggatat gaggta                36

<210> SEQ ID NO 24
<211> LENGTH: 37
<212> TYPE: DNA
<213> ORGANISM: Artificial Sequence
<220> FEATURE:
<223> OTHER INFORMATION: NotI F primer for HisG1

<400> SEQUENCE: 24
tgtttctcgg cggccgccag accggttcag acaggat                37

<210> SEQ ID NO 25
<211> LENGTH: 36
<212> TYPE: DNA
<213> ORGANISM: Artificial Sequence
<220> FEATURE:
<223> OTHER INFORMATION: BamHI R primer for HisG1

<400> SEQUENCE: 25
tccaacgcgt ggatccggag gtgcggatat gaggta                36

<210> SEQ ID NO 26
<211> LENGTH: 36
<212> TYPE: DNA
<213> ORGANISM: Artificial Sequence
<220> FEATURE:
<223> OTHER INFORMATION: BglII F primer for HisG2

<400> SEQUENCE: 26
aattgggccc agatctaacg ctacctcgac cagaaa                36

<210> SEQ ID NO 27
<211> LENGTH: 36
<212> TYPE: DNA
<213> ORGANISM: Artificial Sequence
<220> FEATURE:
<223> OTHER INFORMATION: EcoRI R primer for HisG2

<400> SEQUENCE: 27
tctctgggcg gaattctctt ctcgatcggc agtacc                              36

<210> SEQ ID NO 28
<211> LENGTH: 37
<212> TYPE: DNA
<213> ORGANISM: Artificial Sequence
<220> FEATURE:
<223> OTHER INFORMATION: NotI F primer for HisG2

<400> SEQUENCE: 28
tgtttctcgg cggccgcaac gctacctcga ccagaaa                             37

<210> SEQ ID NO 29
<211> LENGTH: 36
<212> TYPE: DNA
<213> ORGANISM: Artificial Sequence
<220> FEATURE:
<223> OTHER INFORMATION: BamHI R primer for HisG2

<400> SEQUENCE: 29
tccaacgcgt ggatcctctt ctcgatcggc agtacc                              36

<210> SEQ ID NO 30
<211> LENGTH: 36
<212> TYPE: DNA
<213> ORGANISM: Artificial Sequence
<220> FEATURE:
<223> OTHER INFORMATION: BglII F primer for glt2

<400> SEQUENCE: 30
aattgggccc agatcttcag aacttgcgcc gataaa                              36

<210> SEQ ID NO 31
<211> LENGTH: 38
<212> TYPE: DNA
<213> ORGANISM: Artificial Sequence
<220> FEATURE:
<223> OTHER INFORMATION: EcoRI R primer for glt2

<400> SEQUENCE: 31
tctctgggcg gaattccttt gccagctaga ccatagag                            38

<210> SEQ ID NO 32
<211> LENGTH: 37
<212> TYPE: DNA
<213> ORGANISM: Artificial Sequence
<220> FEATURE:
<223> OTHER INFORMATION: NotI F primer for glt2

<400> SEQUENCE: 32
tgtttctcgg cggccgctca gaacttgcgc cgataaa                             37

<210> SEQ ID NO 33
<211> LENGTH: 38
<212> TYPE: DNA
<213> ORGANISM: Artificial Sequence
<220> FEATURE:
<223> OTHER INFORMATION: BamHI R primer for glt2

```
<400> SEQUENCE: 33
tccaacgcgt ggatcccttt gccagctaga ccatagag                              38

<210> SEQ ID NO 34
<211> LENGTH: 35
<212> TYPE: DNA
<213> ORGANISM: Artificial Sequence
<220> FEATURE:
<223> OTHER INFORMATION: BglII F primer for glt3

<400> SEQUENCE: 34
aattgggccc agatctattg gcgggttcgt tactt                                 35

<210> SEQ ID NO 35
<211> LENGTH: 38
<212> TYPE: DNA
<213> ORGANISM: Artificial Sequence
<220> FEATURE:
<223> OTHER INFORMATION: EcoRI R primer for glt3

<400> SEQUENCE: 35
tctctgggcg gaattccctg gaagaaggcc gtattatc                              38

<210> SEQ ID NO 36
<211> LENGTH: 36
<212> TYPE: DNA
<213> ORGANISM: Artificial Sequence
<220> FEATURE:
<223> OTHER INFORMATION: NotI F primer for glt3

<400> SEQUENCE: 36
tgtttctcgg cggccgcatt ggcgggttcg ttactt                                36

<210> SEQ ID NO 37
<211> LENGTH: 38
<212> TYPE: DNA
<213> ORGANISM: Artificial Sequence
<220> FEATURE:
<223> OTHER INFORMATION: BamHI R primer for glt3

<400> SEQUENCE: 37
tccaacgcgt ggatcccctg gaagaaggcc gtattatc                              38

<210> SEQ ID NO 38
<211> LENGTH: 20
<212> TYPE: DNA
<213> ORGANISM: Artificial Sequence
<220> FEATURE:
<223> OTHER INFORMATION: F1 primer for ACO1

<400> SEQUENCE: 38
ttcctcaatg gtggagaaga                                                  20

<210> SEQ ID NO 39
<211> LENGTH: 46
<212> TYPE: DNA
<213> ORGANISM: Artificial Sequence
<220> FEATURE:
<223> OTHER INFORMATION: R1 primer for ACO1

<400> SEQUENCE: 39
tctttatcct gtctgaaccg gtctggtacc atagtccttg ccatgc                     46

<210> SEQ ID NO 40
```

```
<211> LENGTH: 45
<212> TYPE: DNA
<213> ORGANISM: Artificial Sequence
<220> FEATURE:
<223> OTHER INFORMATION: F2 primer for ACO1

<400> SEQUENCE: 40
atcgctacct catatccgca cctcccttct gtcccccgag tttct          45

<210> SEQ ID NO 41
<211> LENGTH: 19
<212> TYPE: DNA
<213> ORGANISM: Artificial Sequence
<220> FEATURE:
<223> OTHER INFORMATION: R2 primer for ACO1

<400> SEQUENCE: 41
aagaagggct tgagagtcg                                       19

<210> SEQ ID NO 42
<211> LENGTH: 17
<212> TYPE: DNA
<213> ORGANISM: Artificial Sequence
<220> FEATURE:
<223> OTHER INFORMATION: F1 primer for ACO2

<400> SEQUENCE: 42
cccaacaaca ctggcac                                         17

<210> SEQ ID NO 43
<211> LENGTH: 43
<212> TYPE: DNA
<213> ORGANISM: Artificial Sequence
<220> FEATURE:
<223> OTHER INFORMATION: R1 primer for ACO2

<400> SEQUENCE: 43
tctttatcct gtctgaaccg gtctgctcct catcgtagat ggc            43

<210> SEQ ID NO 44
<211> LENGTH: 42
<212> TYPE: DNA
<213> ORGANISM: Artificial Sequence
<220> FEATURE:
<223> OTHER INFORMATION: F2 primer for ACO2

<400> SEQUENCE: 44
atcgctacct catatccgca cctccgacaa gacccgacag gc             42

<210> SEQ ID NO 45
<211> LENGTH: 18
<212> TYPE: DNA
<213> ORGANISM: Artificial Sequence
<220> FEATURE:
<223> OTHER INFORMATION: R2 primer for ACO2

<400> SEQUENCE: 45
agaccagagt cctcttcg                                        18

<210> SEQ ID NO 46
<211> LENGTH: 19
<212> TYPE: DNA
<213> ORGANISM: Artificial Sequence
<220> FEATURE:
<223> OTHER INFORMATION: F1 primer for ACO3

<400> SEQUENCE: 46
```
accttcacag agccaccca                                          19

<210> SEQ ID NO 47
<211> LENGTH: 36
<212> TYPE: DNA
<213> ORGANISM: Artificial Sequence
<220> FEATURE:
<223> OTHER INFORMATION: R1 primer for ACO3

<400> SEQUENCE: 47
atggctctct gggcggtgtt gggggtgttg atgatg                       36

<210> SEQ ID NO 48
<211> LENGTH: 36
<212> TYPE: DNA
<213> ORGANISM: Artificial Sequence
<220> FEATURE:
<223> OTHER INFORMATION: F2 primer for ACO3

<400> SEQUENCE: 48
ttgttgtgtt tctcgcaagg ttctcatcga ggcctg                       36

<210> SEQ ID NO 49
<211> LENGTH: 22
<212> TYPE: DNA
<213> ORGANISM: Artificial Sequence
<220> FEATURE:
<223> OTHER INFORMATION: R2 primer for ACO3

<400> SEQUENCE: 49
aggaaaggtc gaagagtgct ct                                      22

<210> SEQ ID NO 50
<211> LENGTH: 17
<212> TYPE: DNA
<213> ORGANISM: Artificial Sequence
<220> FEATURE:
<223> OTHER INFORMATION: F1 primer for ACO4

<400> SEQUENCE: 50
actgcgagag cgatctg                                            17

<210> SEQ ID NO 51
<211> LENGTH: 45
<212> TYPE: DNA
<213> ORGANISM: Artificial Sequence
<220> FEATURE:
<223> OTHER INFORMATION: R1 primer for ACO4

<400> SEQUENCE: 51
tctttatcct gtctgaaccg gtctgttcat gagcatgtag tttcg             45

<210> SEQ ID NO 52
<211> LENGTH: 44
<212> TYPE: DNA
<213> ORGANISM: Artificial Sequence
<220> FEATURE:
<223> OTHER INFORMATION: F2 primer for ACO4

<400> SEQUENCE: 52
atcgctacct catatccgca cctccgagga cgacaaagcc ggag              44

<210> SEQ ID NO 53
<211> LENGTH: 19
<212> TYPE: DNA

```
<213> ORGANISM: Artificial Sequence
<220> FEATURE:
<223> OTHER INFORMATION: R2 primer for ACO4

<400> SEQUENCE: 53
agagcagagt cctcctcaa                                              19

<210> SEQ ID NO 54
<211> LENGTH: 22
<212> TYPE: DNA
<213> ORGANISM: Artificial Sequence
<220> FEATURE:
<223> OTHER INFORMATION: F1 primer for ACO5

<400> SEQUENCE: 54
aacttcctca caggcagcga gc                                          22

<210> SEQ ID NO 55
<211> LENGTH: 39
<212> TYPE: DNA
<213> ORGANISM: Artificial Sequence
<220> FEATURE:
<223> OTHER INFORMATION: R1 primer for ACO5

<400> SEQUENCE: 55
atggctctct gggcggagta gagagtggga gttgaggtc                        39

<210> SEQ ID NO 56
<211> LENGTH: 34
<212> TYPE: DNA
<213> ORGANISM: Artificial Sequence
<220> FEATURE:
<223> OTHER INFORMATION: F2 primer for ACO5

<400> SEQUENCE: 56
ttgttgtgtt tctcgccccg tcaaggacgc tgag                             34

<210> SEQ ID NO 57
<211> LENGTH: 22
<212> TYPE: DNA
<213> ORGANISM: Artificial Sequence
<220> FEATURE:
<223> OTHER INFORMATION: R2 primer for ACO5

<400> SEQUENCE: 57
acagtaaggt ggggcttgac tc                                          22

<210> SEQ ID NO 58
<211> LENGTH: 21
<212> TYPE: DNA
<213> ORGANISM: Artificial Sequence
<220> FEATURE:
<223> OTHER INFORMATION: F1 primer for ACO6

<400> SEQUENCE: 58
agtccctcaa cacgtttacc g                                           21

<210> SEQ ID NO 59
<211> LENGTH: 46
<212> TYPE: DNA
<213> ORGANISM: Artificial Sequence
<220> FEATURE:
<223> OTHER INFORMATION: R1 primer for ACO6

<400> SEQUENCE: 59
tctttatcct gtctgaaccg gtctgccatt tagtggcagc aacgtt                46
```

<210> SEQ ID NO 60
<211> LENGTH: 45
<212> TYPE: DNA
<213> ORGANISM: Artificial Sequence
<220> FEATURE:
<223> OTHER INFORMATION: F2 primer for ACO6

<400> SEQUENCE: 60
atcgctacct catatccgca cctccgagct ctgatcaacc gaacc          45

<210> SEQ ID NO 61
<211> LENGTH: 20
<212> TYPE: DNA
<213> ORGANISM: Artificial Sequence
<220> FEATURE:
<223> OTHER INFORMATION: R2 primer for ACO6

<400> SEQUENCE: 61
aggaagggtc taatgacaga                                       20

<210> SEQ ID NO 62
<211> LENGTH: 17
<212> TYPE: DNA
<213> ORGANISM: Artificial Sequence
<220> FEATURE:
<223> OTHER INFORMATION: F1 primer for FALDH1

<400> SEQUENCE: 62
aatcactcct cctacgc                                          17

<210> SEQ ID NO 63
<211> LENGTH: 43
<212> TYPE: DNA
<213> ORGANISM: Artificial Sequence
<220> FEATURE:
<223> OTHER INFORMATION: R1 primer for FALDH1

<400> SEQUENCE: 63
tctttatcct gtctgaaccg gtctgtggtc tcggggacac ctc             43

<210> SEQ ID NO 64
<211> LENGTH: 43
<212> TYPE: DNA
<213> ORGANISM: Artificial Sequence
<220> FEATURE:
<223> OTHER INFORMATION: F2 primer for FALDH1

<400> SEQUENCE: 64
atcgctacct catatccgca cctccccatc atcaagcccc gaa             43

<210> SEQ ID NO 65
<211> LENGTH: 20
<212> TYPE: DNA
<213> ORGANISM: Artificial Sequence
<220> FEATURE:
<223> OTHER INFORMATION: R2 primer for FALDH1

<400> SEQUENCE: 65
accgacataa tctgagcaat                                       20

<210> SEQ ID NO 66
<211> LENGTH: 19
<212> TYPE: DNA
<213> ORGANISM: Artificial Sequence
<220> FEATURE:

<223> OTHER INFORMATION: F1 primer for FALDH2

<400> SEQUENCE: 66
accactaggt gagatcgag                                                19

<210> SEQ ID NO 67
<211> LENGTH: 45
<212> TYPE: DNA
<213> ORGANISM: Artificial Sequence
<220> FEATURE:
<223> OTHER INFORMATION: R1 primer for FALDH2

<400> SEQUENCE: 67
tctttatcct gtctgaaccg gtctgctccg acactaccgg aacgc                   45

<210> SEQ ID NO 68
<211> LENGTH: 43
<212> TYPE: DNA
<213> ORGANISM: Artificial Sequence
<220> FEATURE:
<223> OTHER INFORMATION: F2 primer for FALDH2

<400> SEQUENCE: 68
atcgctacct catatccgca cctcccttgc tcccacagtt gtt                     43

<210> SEQ ID NO 69
<211> LENGTH: 19
<212> TYPE: DNA
<213> ORGANISM: Artificial Sequence
<220> FEATURE:
<223> OTHER INFORMATION: R2 primer for FALDH2

<400> SEQUENCE: 69
gatcacccag aaccatagc                                                19

<210> SEQ ID NO 70
<211> LENGTH: 19
<212> TYPE: DNA
<213> ORGANISM: Artificial Sequence
<220> FEATURE:
<223> OTHER INFORMATION: F1 primer for FALDH3

<400> SEQUENCE: 70
gtgaccccca ccacgtcac                                                19

<210> SEQ ID NO 71
<211> LENGTH: 46
<212> TYPE: DNA
<213> ORGANISM: Artificial Sequence
<220> FEATURE:
<223> OTHER INFORMATION: R1 primer for FALDH3

<400> SEQUENCE: 71
tctttatcct gtctgaaccg gtctgttctg acattttcag cgccac                  46

<210> SEQ ID NO 72
<211> LENGTH: 45
<212> TYPE: DNA
<213> ORGANISM: Artificial Sequence
<220> FEATURE:
<223> OTHER INFORMATION: F2 primer for FALDH3

<400> SEQUENCE: 72
atcgctacct catatccgca cctcccatt acgagcgttt gacgg                    45

```
<210> SEQ ID NO 73
<211> LENGTH: 17
<212> TYPE: DNA
<213> ORGANISM: Artificial Sequence
<220> FEATURE:
<223> OTHER INFORMATION: R2 primer for FALDH3

<400> SEQUENCE: 73
cagggctggg gaccacc                                                    17

<210> SEQ ID NO 74
<211> LENGTH: 19
<212> TYPE: DNA
<213> ORGANISM: Artificial Sequence
<220> FEATURE:
<223> OTHER INFORMATION: F1 primer for FALDH4

<400> SEQUENCE: 74
taccgactgg accagattc                                                  19

<210> SEQ ID NO 75
<211> LENGTH: 46
<212> TYPE: DNA
<213> ORGANISM: Artificial Sequence
<220> FEATURE:
<223> OTHER INFORMATION: R1 primer for FALDH4

<400> SEQUENCE: 75
tctttatcct gtctgaaccg gtctgcggca gtggcaatga tcttac                    46

<210> SEQ ID NO 76
<211> LENGTH: 46
<212> TYPE: DNA
<213> ORGANISM: Artificial Sequence
<220> FEATURE:
<223> OTHER INFORMATION: F2 primer for FALDH4

<400> SEQUENCE: 76
atcgctacct catatccgca cctccgactc gattcatcgc tcctac                    46

<210> SEQ ID NO 77
<211> LENGTH: 21
<212> TYPE: DNA
<213> ORGANISM: Artificial Sequence
<220> FEATURE:
<223> OTHER INFORMATION: R2 primer for FALDH4

<400> SEQUENCE: 77
caaatctttc ggaagattcg g                                               21

<210> SEQ ID NO 78
<211> LENGTH: 20
<212> TYPE: DNA
<213> ORGANISM: Artificial Sequence
<220> FEATURE:
<223> OTHER INFORMATION: F1 primer for FAO1

<400> SEQUENCE: 78
atcattgtcg gtggaggaac                                                 20

<210> SEQ ID NO 79
<211> LENGTH: 45
<212> TYPE: DNA
<213> ORGANISM: Artificial Sequence
<220> FEATURE:
<223> OTHER INFORMATION: R1 primer for FAO1
```

<400> SEQUENCE: 79
acgcctttct ggtcgaggta gcgttgcgta gtcgtaaggc tggac        45

<210> SEQ ID NO 80
<211> LENGTH: 45
<212> TYPE: DNA
<213> ORGANISM: Artificial Sequence
<220> FEATURE:
<223> OTHER INFORMATION: F2 primer for FAO1

<400> SEQUENCE: 80
attctggtac tgccgatcga aagaccgtc atcggtgaga ttctt        45

<210> SEQ ID NO 81
<211> LENGTH: 20
<212> TYPE: DNA
<213> ORGANISM: Artificial Sequence
<220> FEATURE:
<223> OTHER INFORMATION: R2 primer for FAO1

<400> SEQUENCE: 81
attcgaggtc ggagatcctt        20

<210> SEQ ID NO 82
<211> LENGTH: 20
<212> TYPE: DNA
<213> ORGANISM: Artificial Sequence
<220> FEATURE:
<223> OTHER INFORMATION: F1 primer for ADH1

<400> SEQUENCE: 82
cccagaaggc tgtcattttc        20

<210> SEQ ID NO 83
<211> LENGTH: 45
<212> TYPE: DNA
<213> ORGANISM: Artificial Sequence
<220> FEATURE:
<223> OTHER INFORMATION: R1 primer for ADH1

<400> SEQUENCE: 83
acgcctttct ggtcgaggta gcgtttcgca gttcttgggg atatg        45

<210> SEQ ID NO 84
<211> LENGTH: 45
<212> TYPE: DNA
<213> ORGANISM: Artificial Sequence
<220> FEATURE:
<223> OTHER INFORMATION: F2 primer for ADH1

<400> SEQUENCE: 84
attctggtac tgccgatcga aagagccga caaggagaag atgtg        45

<210> SEQ ID NO 85
<211> LENGTH: 19
<212> TYPE: DNA
<213> ORGANISM: Artificial Sequence
<220> FEATURE:
<223> OTHER INFORMATION: R2 primer for ADH1

<400> SEQUENCE: 85
caatcttgcc ctcctccat        19

<210> SEQ ID NO 86
<211> LENGTH: 20

<212> TYPE: DNA
<213> ORGANISM: Artificial Sequence
<220> FEATURE:
<223> OTHER INFORMATION: F1 primer for ADH2

<400> SEQUENCE: 86
ccagaagggt gtcatcttcg                                                   20

<210> SEQ ID NO 87
<211> LENGTH: 45
<212> TYPE: DNA
<213> ORGANISM: Artificial Sequence
<220> FEATURE:
<223> OTHER INFORMATION: R1 primer for ADH2

<400> SEQUENCE: 87
acgcctttct ggtcgaggta gcgttatcgc agttcttggg aatgt                       45

<210> SEQ ID NO 88
<211> LENGTH: 45
<212> TYPE: DNA
<213> ORGANISM: Artificial Sequence
<220> FEATURE:
<223> OTHER INFORMATION: F2 primer for ADH2

<400> SEQUENCE: 88
attctggtac tgccgatcga gaagaccgac aaggagaaga tgtgc                       45

<210> SEQ ID NO 89
<211> LENGTH: 20
<212> TYPE: DNA
<213> ORGANISM: Artificial Sequence
<220> FEATURE:
<223> OTHER INFORMATION: R2 primer for ADH2

<400> SEQUENCE: 89
caatcttgcc ctcctccata                                                   20

<210> SEQ ID NO 90
<211> LENGTH: 20
<212> TYPE: DNA
<213> ORGANISM: Artificial Sequence
<220> FEATURE:
<223> OTHER INFORMATION: F1 primer for ADH3

<400> SEQUENCE: 90
agaaagccgt catcttcgag                                                   20

<210> SEQ ID NO 91
<211> LENGTH: 45
<212> TYPE: DNA
<213> ORGANISM: Artificial Sequence
<220> FEATURE:
<223> OTHER INFORMATION: R1 primer for ADH3

<400> SEQUENCE: 91
ttgcacaagt aacgaacccg ccaattcaca gttcttgggg atgtg                       45

<210> SEQ ID NO 92
<211> LENGTH: 46
<212> TYPE: DNA
<213> ORGANISM: Artificial Sequence
<220> FEATURE:
<223> OTHER INFORMATION: F2 primer for ADH3

<400> SEQUENCE: 92
ggagataata cggccttctt ccagggctga caaggagaag atgtgc       46

<210> SEQ ID NO 93
<211> LENGTH: 20
<212> TYPE: DNA
<213> ORGANISM: Artificial Sequence
<220> FEATURE:
<223> OTHER INFORMATION: R2 primer for ADH3

<400> SEQUENCE: 93
acttggagca gtccagaacg       20

<210> SEQ ID NO 94
<211> LENGTH: 20
<212> TYPE: DNA
<213> ORGANISM: Artificial Sequence
<220> FEATURE:
<223> OTHER INFORMATION: F1 primer for ADH4

<400> SEQUENCE: 94
gtcaaaacgt cgacgaacct       20

<210> SEQ ID NO 95
<211> LENGTH: 45
<212> TYPE: DNA
<213> ORGANISM: Artificial Sequence
<220> FEATURE:
<223> OTHER INFORMATION: R1 primer for ADH4

<400> SEQUENCE: 95
aggtatttat cggcgcaagt tctgaggctt gaggtcaatg tcgat       45

<210> SEQ ID NO 96
<211> LENGTH: 45
<212> TYPE: DNA
<213> ORGANISM: Artificial Sequence
<220> FEATURE:
<223> OTHER INFORMATION: F2 primer for ADH4

<400> SEQUENCE: 96
ctcctctatg gtctagctgg caaaggacat ggaggcccac tctaa       45

<210> SEQ ID NO 97
<211> LENGTH: 20
<212> TYPE: DNA
<213> ORGANISM: Artificial Sequence
<220> FEATURE:
<223> OTHER INFORMATION: R2 primer for ADH4

<400> SEQUENCE: 97
agtactccca agcgtcctca       20

<210> SEQ ID NO 98
<211> LENGTH: 18
<212> TYPE: DNA
<213> ORGANISM: Artificial Sequence
<220> FEATURE:
<223> OTHER INFORMATION: F1 primer for ADH5

<400> SEQUENCE: 98
gagagccgct ttcaccac       18

<210> SEQ ID NO 99
<211> LENGTH: 45
<212> TYPE: DNA
<213> ORGANISM: Artificial Sequence

```
<220> FEATURE:
<223> OTHER INFORMATION: R1 primer for ADH5

<400> SEQUENCE: 99
aggtatttat cggcgcaagt tctgaagagc ctggtaggca gtgag            45

<210> SEQ ID NO 100
<211> LENGTH: 45
<212> TYPE: DNA
<213> ORGANISM: Artificial Sequence
<220> FEATURE:
<223> OTHER INFORMATION: F2 primer for ADH5

<400> SEQUENCE: 100
ctcctctatg gtctagctgg caaagttcca ggacgtgatc aagga            45

<210> SEQ ID NO 101
<211> LENGTH: 21
<212> TYPE: DNA
<213> ORGANISM: Artificial Sequence
<220> FEATURE:
<223> OTHER INFORMATION: R2 primer for ADH5

<400> SEQUENCE: 101
taaggatgat cttgccggta g                                      21

<210> SEQ ID NO 102
<211> LENGTH: 20
<212> TYPE: DNA
<213> ORGANISM: Artificial Sequence
<220> FEATURE:
<223> OTHER INFORMATION: F1 primer for ADH6

<400> SEQUENCE: 102
gacccagaaa gccattgtgt                                        20

<210> SEQ ID NO 103
<211> LENGTH: 45
<212> TYPE: DNA
<213> ORGANISM: Artificial Sequence
<220> FEATURE:
<223> OTHER INFORMATION: R1 primer for ADH6

<400> SEQUENCE: 103
aggtatttat cggcgcaagt tctgaagcca cctgagaaag gtctg            45

<210> SEQ ID NO 104
<211> LENGTH: 45
<212> TYPE: DNA
<213> ORGANISM: Artificial Sequence
<220> FEATURE:
<223> OTHER INFORMATION: F2 primer for ADH6

<400> SEQUENCE: 104
ctcctctatg gtctagctgg caaagcaccg aggagaagga gaaga            45

<210> SEQ ID NO 105
<211> LENGTH: 20
<212> TYPE: DNA
<213> ORGANISM: Artificial Sequence
<220> FEATURE:
<223> OTHER INFORMATION: R2 primer for ADH6

<400> SEQUENCE: 105
tccctcctcc atcaaggtaa                                        20
```

<210> SEQ ID NO 106
<211> LENGTH: 21
<212> TYPE: DNA
<213> ORGANISM: Artificial Sequence
<220> FEATURE:
<223> OTHER INFORMATION: F1 primer for ADH7

<400> SEQUENCE: 106
gacgttccca agacacaaaa g                                     21

<210> SEQ ID NO 107
<211> LENGTH: 45
<212> TYPE: DNA
<213> ORGANISM: Artificial Sequence
<220> FEATURE:
<223> OTHER INFORMATION: R1 primer for ADH7

<400> SEQUENCE: 107
aggtatttat cggcgcaagt tctgaaggcg tactgctgga aagag           45

<210> SEQ ID NO 108
<211> LENGTH: 43
<212> TYPE: DNA
<213> ORGANISM: Artificial Sequence
<220> FEATURE:
<223> OTHER INFORMATION: F2 primer for ADH7

<400> SEQUENCE: 108
ctcctctatg gtctagctgg caaagaccca caccaaggag ctg             43

<210> SEQ ID NO 109
<211> LENGTH: 20
<212> TYPE: DNA
<213> ORGANISM: Artificial Sequence
<220> FEATURE:
<223> OTHER INFORMATION: R2 primer for ADH7

<400> SEQUENCE: 109
caacgacacg accaacaatc                                       20

<210> SEQ ID NO 110
<211> LENGTH: 20
<212> TYPE: DNA
<213> ORGANISM: Artificial Sequence
<220> FEATURE:
<223> OTHER INFORMATION: F1 primer for ADH8

<400> SEQUENCE: 110
atcgcgccaa cttgtttaat                                       20

<210> SEQ ID NO 111
<211> LENGTH: 45
<212> TYPE: DNA
<213> ORGANISM: Artificial Sequence
<220> FEATURE:
<223> OTHER INFORMATION: R1 primer for ADH8

<400> SEQUENCE: 111
aggtatttat cggcgcaagt tctgacacct tctctcgtgg gatgt           45

<210> SEQ ID NO 112
<211> LENGTH: 45
<212> TYPE: DNA
<213> ORGANISM: Artificial Sequence
<220> FEATURE:
<223> OTHER INFORMATION: F2 primer for ADH8

```
<400> SEQUENCE: 112
ctcctctatg gtctagctgg caaagtgtgt tgagtctggc aaagc            45

<210> SEQ ID NO 113
<211> LENGTH: 20
<212> TYPE: DNA
<213> ORGANISM: Artificial Sequence
<220> FEATURE:
<223> OTHER INFORMATION: R2 primer for ADH8

<400> SEQUENCE: 113
tcaagtccat ggcatcaaac                                        20

<210> SEQ ID NO 114
<211> LENGTH: 20
<212> TYPE: DNA
<213> ORGANISM: Artificial Sequence
<220> FEATURE:
<223> OTHER INFORMATION: F1 primer for FADH

<400> SEQUENCE: 114
ccgaaggaaa gaccatcact                                        20

<210> SEQ ID NO 115
<211> LENGTH: 45
<212> TYPE: DNA
<213> ORGANISM: Artificial Sequence
<220> FEATURE:
<223> OTHER INFORMATION: R1 primer for FADH

<400> SEQUENCE: 115
ttgcacaagt aacgaacccg ccaatagaag gaagagcagc ccata            45

<210> SEQ ID NO 116
<211> LENGTH: 45
<212> TYPE: DNA
<213> ORGANISM: Artificial Sequence
<220> FEATURE:
<223> OTHER INFORMATION: F2 primer for FADH

<400> SEQUENCE: 116
ggagataata cggccttctt ccagggcttg ggcttacaag tttgg            45

<210> SEQ ID NO 117
<211> LENGTH: 20
<212> TYPE: DNA
<213> ORGANISM: Artificial Sequence
<220> FEATURE:
<223> OTHER INFORMATION: R2 primer for FADH

<400> SEQUENCE: 117
tcggtgaagg cagagttgat                                        20

<210> SEQ ID NO 118
<211> LENGTH: 20
<212> TYPE: DNA
<213> ORGANISM: Artificial Sequence
<220> FEATURE:
<223> OTHER INFORMATION: F primer for HISG1

<400> SEQUENCE: 118
cagaccggtt cagacaggat                                        20

<210> SEQ ID NO 119
```

```
<211> LENGTH: 20
<212> TYPE: DNA
<213> ORGANISM: Artificial Sequence
<220> FEATURE:
<223> OTHER INFORMATION: R primer for HISG1

<400> SEQUENCE: 119
ggaggtgcgg atatgaggta                                              20

<210> SEQ ID NO 120
<211> LENGTH: 20
<212> TYPE: DNA
<213> ORGANISM: Artificial Sequence
<220> FEATURE:
<223> OTHER INFORMATION: F primer for HISG2

<400> SEQUENCE: 120
aacgctacct cgaccagaaa                                              20

<210> SEQ ID NO 121
<211> LENGTH: 20
<212> TYPE: DNA
<213> ORGANISM: Artificial Sequence
<220> FEATURE:
<223> OTHER INFORMATION: R primer for HISG2

<400> SEQUENCE: 121
tcttctcgat cggcagtacc                                              20

<210> SEQ ID NO 122
<211> LENGTH: 20
<212> TYPE: DNA
<213> ORGANISM: Artificial Sequence
<220> FEATURE:
<223> OTHER INFORMATION: F primer for glt2

<400> SEQUENCE: 122
tcagaacttg cgccgataaa                                              20

<210> SEQ ID NO 123
<211> LENGTH: 22
<212> TYPE: DNA
<213> ORGANISM: Artificial Sequence
<220> FEATURE:
<223> OTHER INFORMATION: R primer for glt2

<400> SEQUENCE: 123
ctttgccagc tagaccatag ag                                           22

<210> SEQ ID NO 124
<211> LENGTH: 19
<212> TYPE: DNA
<213> ORGANISM: Artificial Sequence
<220> FEATURE:
<223> OTHER INFORMATION: F primer for glt3

<400> SEQUENCE: 124
attggcgggt tcgttactt                                               19

<210> SEQ ID NO 125
<211> LENGTH: 22
<212> TYPE: DNA
<213> ORGANISM: Artificial Sequence
<220> FEATURE:
<223> OTHER INFORMATION: R primer for glt3

<400> SEQUENCE: 125
```

```
cctggaagaa ggccgtatta tc                                              22

<210> SEQ ID NO 126
<211> LENGTH: 23
<212> TYPE: DNA
<213> ORGANISM: Artificial Sequence
<220> FEATURE:
<223> OTHER INFORMATION: Ulura3 cs 2B primer for Bipartite

<400> SEQUENCE: 126
atgccctcct acgaagctcg agc                                             23

<210> SEQ ID NO 127
<211> LENGTH: 20
<212> TYPE: DNA
<213> ORGANISM: Artificial Sequence
<220> FEATURE:
<223> OTHER INFORMATION: Ylura3F primer for Bipartite

<400> SEQUENCE: 127
ctcccaacga gaagctggcc                                                 20
```